(12) United States Patent
Goel

(10) Patent No.: US 8,049,038 B2
(45) Date of Patent: Nov. 1, 2011

(54) CARNITINE CONJUGATES OF ADAMANTANAMINES DERIVATIVES AS DUAL PRODRUGS FOR VARIOUS USES

(75) Inventor: Om P. Goel, Ann Arbor, MI (US)

(73) Assignee: SSV Therapeutics, Inc., Ann Arbor, MI (US)

( * ) Notice: Subject to any disclaimer, the term of this patent is extended or adjusted under 35 U.S.C. 154(b) by 0 days.

(21) Appl. No.: 13/103,053

(22) Filed: May 7, 2011

(65) Prior Publication Data

US 2011/0212166 A1  Sep. 1, 2011

Related U.S. Application Data

(62) Division of application No. 11/992,907, filed as application No. PCT/US2007/008477 on Apr. 4, 2007, now Pat. No. 7,977,511.

(60) Provisional application No. 60/790,465, filed on Apr. 7, 2006.

(51) Int. Cl.
*C07C 321/00* (2006.01)

(52) U.S. Cl. .................. 564/192; 514/626; 514/511

(58) Field of Classification Search .................. None
See application file for complete search history.

(56) References Cited

U.S. PATENT DOCUMENTS

| | | | |
|---|---|---|---|
| 7,977,511 B2 * | 7/2011 | Goel | 564/192 |
| 2003/0114460 A1 * | 6/2003 | Hughes et al. | 514/249 |
| 2005/0049312 A1 * | 3/2005 | Makovec et al. | 514/631 |

OTHER PUBLICATIONS

Blair Jarvis and David P. Figgitt, "Mementine", Drugs Aging 20(6), 465-476 (2003), Adis Data Information BV 2003.
Barry Reisberg, MD et al., "Memantine in Moderate-to-Severe Alzheimer's Disease", N Engl. J. of Med. 348, 1333-1341 (2003), Mass. Medical Society.
C. G. Parsons et al., Memantine is a Clinically Well Tolerated NMDA Receptor Antagonist—a Review of Preclinical Data, Neutopharmacology 38, 735-767 (1999).
Gordon K. Wilcock, "Memantine for the Treatment of Dementia", The Lancet, Neurology 2, 503-505 (Aug. 2003).
A. Bianchetti et al., "Effects of Acetyl-L-carnitine in Alzheimer's Disease Pateients Unresponsive to AChE-I", Curr. Med. Res. and Opinion 19(4), 350-353 (2003), Librapharm Ltd.
A. Spagnoli, MD et al., "Long-term Acetyl-L-carnitine Treatment in Alzheimer's Disease", Neurology 41, 1726-1732 (1991).
J. David Leander et al., "N-Methyl-D-aspartic acid-induced Lethality in Mice:Selective Antagonism by Phenylcyclidine-like Drugs", Brain Res. 448, 115-120 (1988), Elserier Sci.
C. G. Parsons et al., Neuropharmacology 34(10), 1239-1256 (1995), Elsevier Sci.

* cited by examiner

*Primary Examiner* — Sudhakar Katakam
(74) *Attorney, Agent, or Firm* — Technology Law, PLLC; Karen L. Kimble

(57) ABSTRACT

This invention concerns compounds of adamantanamines and neramexane, including their pharmaceutically-acceptable salts, diesterioisomers, and formulations for treating Alzheimer's related dementias, depression, AIDS related dementias, as antivirals, inflammatory diseases such as rheumatoid arthritis, and cerebral ischemia, hyperlipidemia, and diabetes.

6 Claims, No Drawings

CARNITINE CONJUGATES OF ADAMANTANAMINES DERIVATIVES AS DUAL PRODRUGS FOR VARIOUS USES

This application is a divisional of U.S. application Ser. No. 11/992,907, filed Mar. 31, 2008, which is a 371 application which claims benefit from PCT/US2007/008477, filed Apr. 4, 2007, which claims benefit from U.S. Application 60/790,465, filed Apr. 7, 2006.

FIELD OF THE INVENTION

Amantadine (1-aminoadamantane) is an antiviral agent in clinical use. [See for example, Aldrich, P. E. et al., *J. Med. Chem.* 14, 535-543 (1972).] Memantine (3,5-dimethyl-1-adamantanamine) and its pharmaceutically acceptable salts are approved for the treatment of moderate to severe dementia of the Alzheimer's type when used either alone or in combination with donepezil hydrochloride. A memantine related substance, neramexane (1,3,3,5,5-pentamethylcyclohexylamine), is in clinical trials for similar indications.

The present invention relates to novel carnitine amides and esters conjugates of the adamantane amines and neramexanes as improved agents for the treatment of Alzheimer's disease (AD) and related dementias. The novel compositions of the present invention are useful in enhancing the therapeutic benefits of memantine and neramexane in AD; also, as antivirals, and for use in cardiovascular disease, cerebral ischemia, cancer, diabetes, renal anemia, inflammatory diseases, and gastrointestinal disorders. Furthermore, these conjugates may be used as linkers with other therapeutic agents in delivering drugs to the eye where such conjugates display improved absorption and pharmacokinetics.

BACKGROUND OF THE INVENTION

Dementia of the Alzheimer's type is a chronic, progressive neurodegenerative process with attendant memory loss as the prominent early symptom, which may begin as early as in the $5^{th}$ decade of life. With increasing life spans and aging of the population, AD is a great present and looming public health concern. In AD, acetylcholine transmitting neurons and their target nerve cells are affected. A current treatment to ameliorate the symptoms of AD is to increase the brain levels of neurotransmitter acetylcholine by inhibiting the activity of acetylcholinesterase (AChE), an enzyme which deacetylates and neutralizes the effect of beneficial levels of acetylcholine. Currently approved donepezil hydrochloride is such an agent.

A second mechanism to alleviate the symptoms of AD is to block the excitotoxic neuronal pathways related to excess glutamate release in the central nervous system (CNS). NMDA (N-methyl-D-aspartate) receptors are ionotropic receptors that mediate cellular transport of mono and divalent ions. It is known that excess $Ca^{++}$ ions over normal levels of intracellular $Ca^{++}$ ions results in neurotoxicity and cell death. Excessive excitation of NMDA receptors in the CNS needs to be moderated. [Jarvis, B., et al., *Drugs Aging* 20, 465-476 (2003).]

Memantine is a well-tolerated uncompetitive antagonist of NMDA receptors with moderate affinity towards these receptors. It is approved as an oral therapy for moderate to severe AD symptoms based on the results of a double-blind, placebo controlled study. [See Reisberg, B. et al., *N. Engl. J. Med.* 348, 1333-1341 (2003).] Memantine exerts neuroprotective effects in several models of brain injury in experimental animals. [See for example Parsons, C. G, et al., *Neuropharmacology* 38, 735-767 (1999); and Wilcock, G. K. *Lancet Neurol.* 2, 503-505 (2003).]

Published US 2005/0049312 A1 by F. Makovec, et al., describe preparation and uses of amidine derivatives of adamantanes with neuroprotective and antidepressant activities.

Recently, Hughes and Olejnik [in U.S. Patent Application 2003/0114460] described novel conjugates of memantine to enhance its use in ophthalmic applications which enhance the therapeutic disposition of the therapeutic component.

Levo carnitine (L-carnitine or vitamin $B_T$) belongs to a class of water soluble vitamins which include vitamin B-12, folic acid, biotin, vitamin B-6, and mevalonic acid. L-acetyl carnitine has been shown to benefit Alzheimer's patients who are unresponsive to acetylcholinesterase inhibitors. [See, for example, Bianchetti, A. et al., *Curr. Med. Res. Opin.* 19, 350-353 (2003), Effects of acetyl-L-carnitine in Alzheimer's disease patients unresponsive to acetylcholinesterase inhibitors; Pettegrew, Jay W., et al., U.S. Patent Application 2005/272812, Method for the use of acetyl-L-carnitine for treatment of depressive disorders; and A. Spagnoli et al., *Neurology* 41, 1726-1732 (1991), Long-term acetyl-L-carnitine treatment in Alzheimer's disease.]

In view of the extensive literature devoted to the benefits of L-carnitine derivatives in the treatment of AD symptoms, the present invention uses novel conjugates of these compounds as esters and amides of adamantanamine and neramexane (1,3,3,5,5-cyclohexylamine) derivatives. Also the present invention describes a novel concept referred to as a "double prodrug" approach, which involves the preparation of novel covalent conjugates comprising two or more drugs, and their use in the treatment of various neurological and other disorders. A suitable covalent attachment of two or more of these agents, with or without a linker, will be of significant therapeutic value in that a single molecular entity may have multiple therapeutic effects resulting from diverse, but synergistic mechanisms of action, and controlled release of both drugs in vivo through enzymatic hydrolysis of the conjugate. The concept of the present invention is not limited to only CNS disorders; other therapeutic applications, including cardiovascular, diabetes, cancer, inflammation, and the like are also contemplated. In particular, the compounds of the present invention provide novel and useful linkers to conjugate with numerous drugs useful for treating the diseases of the eye.

DETAILED DESCRIPTION OF THE INVENTION

The present invention discloses a dual prodrug compound, including its pharmaceutically-acceptable salts, of the Formula (I) below,

Formula (I)

wherein:

Z is an alicyclic or polyalicyclic group of the trialicyclic adamantane or monoalicyclic neramexane type as shown below by Formulae (A) and (B), respectively,

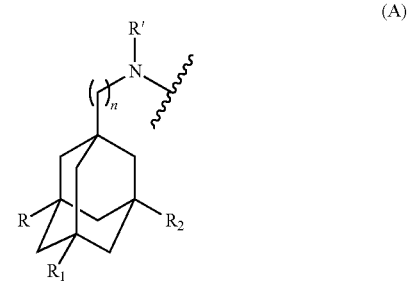

(A)

-continued

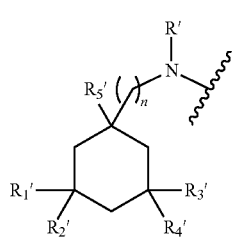
(B)

wherein:

R, $R_1$, $R_2$, $\acute{R}_1$, $\acute{R}_2$, $\acute{R}_3$, $\acute{R}_4$ and $\acute{R}_5$ are each independently H or $CH_3$;

$C_1$-$C_6$ straight chain or branched alkyls, $C_3$-$C_6$ cycloalkyl, $C_2$-$C_6$ alkenyl, $C_2$-$C_6$ alkynyl; $C_6$-$C_{10}$ aryl unsubstituted or substituted with $C_1$-$C_6$ straight chain or branched alkyl, $C_1$-$C_6$ alkoxyl, 1,3-dioxolanyl, cyano, halo, nitro, trihaloalkyl, $C_1$-$C_6$ acyl, $C_1$-$C_6$ dialkylamino, $C_1$-$C_6$ acylamino, $C_1$-$C_6$ mercaptoalkyl; alkylaryl ($C_6$-$C_{10}$), such as a benzyl group unsubstituted or substituted with $C_1$-$C_6$ straight chain or branched alkyl, $C_1$-$C_6$ alkoxyl, 1,3-dioxolanyl, cyano, halo, trihaloalkyl, $C_1$-$C_6$ acyl, $C_1$-$C_6$ dialkylamino, and $C_1$-$C_6$ mercaptoalkyl; and alkyldiaryls such as diphenylmethyl in which the aryls may be bridged by —$CH_2$—$CH_2$— or O or S; where the alkyldiaryls may be unsubstituted or substituted with $C_1$-$C_6$ straight chain or branched alkyl, $C_1$-$C_6$ alkoxyl, 1,3-dioxolanyl, cyano, halo, trihaloalkyl, $C_1$-$C_6$ acyl, $C_1$-$C_6$ dialkylamino, and $C_1$-$C_6$ mercaptoalkyl;

$\acute{R}_1$ and $\acute{R}_2$ may be optionally tethered together to form 3- to 7-membered alicyclic ring;

$\acute{R}_3$ and $\acute{R}_4$ may be optionally tethered together to form 3- to 7-membered alicyclic ring;

n=0 or an integer from 1 through 6;

$\acute{R}$ is H or $C_1$-$C_4$ straight-chain alkyl;

Y is a moiety of Formulae (C), (D), or (E) shown below,

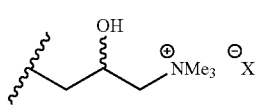
(C)

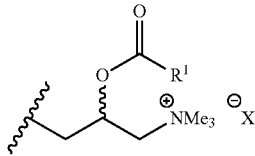
(D)

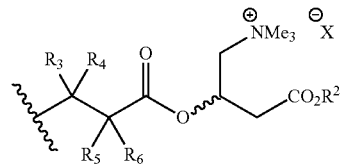
(E)

wherein, $R^1$ is independently selected from the group consisting of straight or branched chain $C_1$-$C_6$ alkyl, $C_3$-$C_6$ cycloalkyl; $C_2$-$C_6$ alkenyl; $C_2$-$C_6$ alkynyl; $C_6$-$C_{10}$ aryl such as phenyl, naphthyl, and the like, or a heteroaryl such as furanyl, imidazolyl, pyrollyl, triazolyl, pyridyl, and the like, unsubstituted or substituted with one or more $C_1$-$C_6$ straight chain or branched alkyl, $C_1$-$C_6$ alkoxyl, 1,3-dioxolanyl, cyano, halo, nitro, trihaloalkyl, $C_1$-$C_6$ acyl, $C_1$-$C_6$ dialkylamino, $C_1$-$C_6$ acylamino, $C_1$-$C_6$ mercaptoalkyl; and straight or branched chain alkylaryl ($C_6$-$C_{10}$), such as a benzyl group, or an alkyl heteroaryl wherein the aryl or the hetroaryl group may be unsubstituted or substituted with one or more $C_1$-$C_6$ straight chain or branched alkyl, $C_1$-$C_6$ alkoxyl, 1,3-dioxolanyl, cyano, halo, trihaloalkyl, $C_1$-$C_6$ acyl, $C_1$-$C_6$ dialkylamino, and $C_1$-$C_6$ mercaptoalkyl, and alkyldiaryls, such as diphenylmethyl in which the aryls may be bridged by —$CH_2$—$CH_2$— or O or S; and the alkyldiaryls may be unsubstituted or substituted with $C_1$-$C_6$ alkyl, $C_1$-$C_6$ alkoxyl, 1,3-dioxolanyl, cyano, halo, trihaloalkyl, $C_1$-$C_6$ acyl, $C_1$-$C_6$ dialkylamino, and $C_1$-$C_6$ mercaptoalkyl;

$X^-$ is a pharmaceutically-acceptable inorganic or organic counter ion;

$R^2$ is hydrogen or an easily cleavable group under acidic or neutral conditions, such as a t-butyl group or an alkylaryl group wherein the aryl group may be unsubstituted or substituted with $C_1$-$C_6$ straight chain or branched alkyl, $C_3$-$C_6$ cycloalkyl, $C_1$-$C_6$ alkoxyl, 1,3-dioxolanyl, and $C_1$-$C_6$ dialkylamino;

$R_3$ to $R_6$ are independently selected from the group consisting of hydrogen; hydroxyl; $C_1$-$C_6$ straight chain or branched alkyl; $C_3$-$C_6$ cycloalkyl; $C_6$-$C_{10}$ aryl, such as phenyl, naphthyl, and the like, unsubstituted or substituted with $C_1$-$C_6$ alkyl, hydroxyl, $C_1$-$C_6$ alkoxyl, 1,3-dioxolanyl, cyano, trihaloalkyl, carboxyl, $C_1$-$C_6$ acyl, $C_1$-$C_6$ hydroxyalkyl, amino, $C_1$-$C_6$ alkylamino, $C_1$-$C_6$ dialkylamino, $C_1$-$C_6$ acylamino, $C_1$-$C_6$ alkylthio, $C_1$-$C_6$ alkoxycarbonyl; and alkylaryl ($C_6$-$C_{10}$) unsubstituted or substituted with $C_1$-$C_6$ alkyl, hydroxyl, $C_1$-$C_6$ alkoxyl, 1,3-dioxolanyl, cyano, trihaloalkyl, carboxyl, $C_1$-$C_6$ acyl, $C_1$-$C_6$ hydroxyalkyl, amino, $C_1$-$C_6$ alkylamino, $C_1$-$C_6$ dialkylamino, $C_1$-$C_6$ alkylthio, $C_1$-$C_6$ alkoxycarbonyl, $C_1$-$C_6$ carboxyalkyl, $C_1$-$C_6$ acylamino, $C_1$-$C_6$ sulfonatoalkyl, $C_1$-$C_6$ sulfamylalkyl, and $C_1$-$C_6$ phosphanatoalkyl;

$R_3$ and $R_4$ may be optionally tethered together to form 3- to 7-membered alicyclic ring; and $R_5$ and $R_6$ may be optionally tethered together to form 3- to 7-membered alicyclic ring.

The preferred embodiments of Formula (I) are shown in Formulae 1-4 and Formulae 5-8, respectively, shown below. In all these compounds R and $\acute{R}$ of Formula (I) are shown as H as a preferred embodiment.

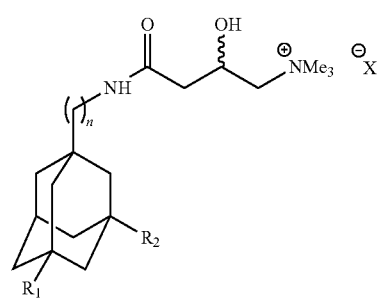

Formula 1 wherein:

$R_1$ and $R_2$ are H or $CH_3$;

$X^-$ is any pharmaceutically-acceptable organic or inorganic counter ion; and n=0, or the integer from 1 through 6.

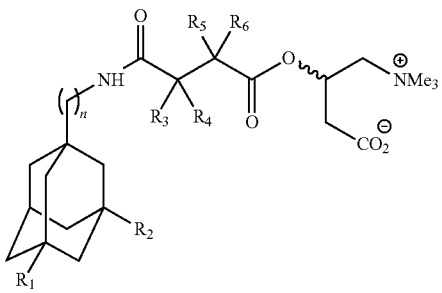

Formula 2 wherein:

$R_1$ and $R_2$ are H or $CH_3$;

n=0, or an integer from 1 through 6;

$R_3$ to $R_6$ are independently selected from the group consisting of hydrogen; hydroxyl; $C_1$-$C_6$ straight chain or branched alkyl; $C_3$-$C_6$ cycloalkyl; $C_6$-$C_{10}$ aryl, such as phenyl, naphthyl, and the like, unsubstituted or substituted with $C_1$-$C_6$ alkyl, hydroxyl, $C_1$-$C_6$ alkoxyl, 1,3-dioxolanyl, cyano, trihaloalkyl, carboxyl, $C_1$-$C_6$ acyl, $C_1$-$C_6$ hydroxyalkyl, amino, $C_1$-$C_6$ alkylamino, $C_1$-$C_6$ dialkylamino, $C_1$-$C_6$ acylamino, $C_1$-$C_6$ alkylthio, $C_1$-$C_6$ alkoxycarbonyl; and alkylaryl ($C_6$-$C_{10}$) unsubstituted or substituted with $C_1$-$C_6$ alkyl, hydroxyl, $C_1$-$C_6$ alkoxyl, 1,3-dioxolanyl, cyano, trihaloalkyl, carboxyl, $C_1$-$C_6$ acyl, $C_1$-$C_6$ hydroxyalkyl, amino, $C_1$-$C_6$ alkylamino, $C_1$-$C_6$ dialkylamino, $C_1$-$C_6$ alkylthio, $C_1$-$C_6$ alkoxycarbonyl, $C_1$-$C_6$ carboxyalkyl, $C_1$-$C_6$ acylamino, $C_1$-$C_6$ sulfonatoalkyl, $C_1$-$C_6$ sulfamylalkyl, and $C_1$-$C_6$ phosphanatoalkyl;

$R_3$ and $R_4$ may be optionally tethered together to form 3- to 7-membered alicyclic ring; and $R_5$ and $R_6$ may be optionally tethered together to form 3- to 7-membered alicyclic ring.

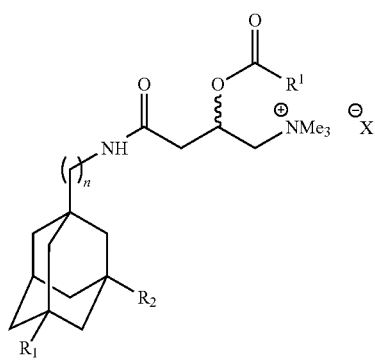

Formula 3 wherein:

$R_1$ and $R_2$ are H or $CH_3$;

$X^-$ is any pharmaceutically-acceptable organic or inorganic counter ion;

n=0, or an integer from 1 through 6;

$R^1$ is independently selected from the group consisting of straight or branched chain $C_1$-$C_6$ alkyl, $C_3$-$C_6$ cycloalkyl; $C_2$-$C_6$ alkenyl; $C_2$-$C_6$ alkynyl; $C_6$-$C_{10}$ aryl such as phenyl, naphthyl and the like, or a heteroaryl such as furanyl, imidazolyl, pyrollyl, triazolyl, pyridyl or the like, unsubstituted or substituted with one or more $C_1$-$C_6$ alkyl, $C_1$-$C_6$ alkoxyl, 1,3-dioxolanyl, cyano, halo, nitro, trihaloalkyl, $C_1$-$C_6$ acyl, $C_1$-$C_6$ dialkylamino, $C_1$-$C_6$ acylamino, $C_1$-$C_6$ mercaptoalkyl; and straight or branched chain alkylaryl ($C_6$-$C_{10}$), such as a benzyl group, or an alkyl heteroaryl wherein the aryl or the hetroaryl group may be unsubstituted or substituted with one or more $C_1$-$C_6$ alkyl, $C_1$-$C_6$ alkoxyl, 1,3-dioxolanyl, cyano, halo, trihaloalkyl, $C_1$-$C_6$ acyl, $C_1$-$C_6$ dialkylamino, and $C_1$-$C_6$ mercaptoalkyl, and alkyldiaryl such as diphenylmethyl in which the aryls may be bridged by —$CH_2$—$CH_2$— or O or S. The alkyldiaryls may be unsubstituted or substituted with $C_1$-$C_6$ alkyl, $C_1$-$C_6$ alkoxyl, 1,3-dioxolanyl, cyano, halo, trihaloalkyl, $C_1$-$C_6$ acyl, $C_1$-$C_6$ dialkylamino, and $C_1$-$C_6$ mercaptoalkyl.

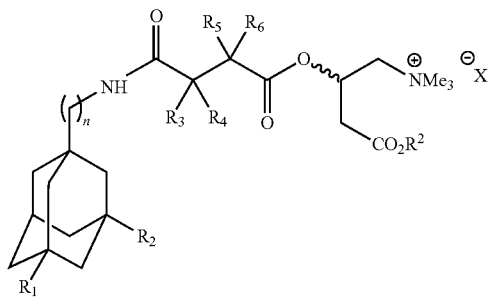

Formula 4 wherein:

$R_1$ and $R_2$ are H or $CH_3$;

$X^-$ is any pharmaceutically-acceptable organic or inorganic counter ion;

n=0, or an integer from 1 through 6;

$R_3$ to $R_6$ are independently selected from the group consisting of hydrogen, hydroxyl, $C_1$-$C_6$ straight chain or branched alkyl; $C_3$-$C_6$ cycloalkyl; $C_6$-$C_{10}$ aryl, such as a phenyl or naphthyl group, unsubstituted or substituted with $C_1$-$C_6$ alkyl, hydroxyl, $C_1$-$C_6$ alkoxyl, 1,3-dioxolanyl, cyano, trihaloalkyl, carboxyl, $C_1$-$C_6$ acyl, $C_1$-$C_6$ hydroxyalkyl, amino, $C_1$-$C_6$ alkylamino, $C_1$-$C_6$ dialkylamino, $C_1$-$C_6$ acylamino, $C_1$-$C_6$ alkylthio, $C_1$-$C_6$ alkoxycarbonyl; and $C_5$-$C_6$ arylalkyl unsubstituted or substituted with $C_1$-$C_6$ alkyl, hydroxyl, $C_1$-$C_6$ alkoxyl, 1,3-dioxolanyl, cyano, trihaloalkyl, carboxyl, $C_1$-$C_6$ acyl, $C_1$-$C_6$ hydroxyalkyl, amino, $C_1$-$C_6$ alkylamino, $C_1$-$C_6$ dialkylamino, $C_1$-$C_6$ alkylthio, $C_1$-$C_6$ alkoxycarbonyl, $C_1$-$C_6$ carboxyalkyl, $C_1$-$C_6$ acylamino, $C_1$-$C_6$ sulfonatoalkyl, $C_1$-$C_6$ sulfamylalkyl, and $C_1$-$C_6$ phosphanatoalkyl;

$R_3$ and $R_4$ may be optionally tethered together to form 3- to 7-membered alicyclic ring; and $R_5$ and $R_6$ may be optionally tethered together to form 3- to 7-membered alicyclic ring; and $R^2$ is hydrogen or an easily cleavable group under acidic or neutral conditions, such as a t-butyl group or an alkylaryl group wherein the aryl group may be unsubstituted or substituted with $C_1$-$C_6$ straight chain or branched alkyl, $C_3$-$C_6$ cycloalkyl, $C_1$-$C_6$ alkoxyls, 1,3-dioxolanyl, and $C_1$-$C_6$ dialkylamino.

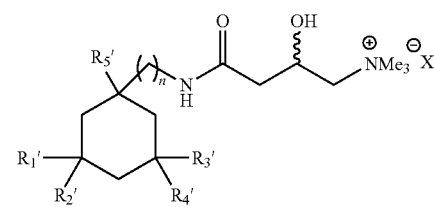

Formula 5 wherein:

Ŕ₁, Ŕ₂, Ŕ₃, Ŕ₄ and Ŕ₅ are independently H or CH₃;

$C_1$-$C_6$ straight chain or branched alkyls, $C_3$-$C_6$ cycloalkyl, $C_2$-$C_6$ alkenyl, $C_2$-$C_6$ alkynyl; $C_6$-$C_{10}$ aryl unsubstituted or substituted with $C_1$-$C_6$ straight chain or branched alkyl, $C_1$-$C_6$ alkoxyl, 1,3-dioxolanyl, cyano, halo, nitro, trihaloalkyl, $C_1$-$C_6$ acyl, $C_1$-$C_6$ dialkylamino, $C_1$-$C_6$ acylamino, $C_1$-$C_6$ mercaptoalkyl; and alkylaryl ($C_6$-$C_{10}$), such as a benzyl group unsubstituted or substituted with $C_1$-$C_6$ alkyl, $C_1$-$C_6$ alkoxyl, 1,3-dioxolanyl, cyano, halo, trihaloalkyl, $C_1$-$C_6$ acyl, $C_1$-$C_6$ dialkylamino, and $C_1$-$C_6$ mercaptoalkyl;

Ŕ₁ and Ŕ₂ may be optionally tethered together to form 3- to 7-membered alicyclic ring;

Ŕ₃ and Ŕ₄ may be optionally tethered together to form 3- to 7-membered alicyclic ring;

n=0 or 1; and $X^-$ is a pharmaceutically-acceptable inorganic or organic counter ion.

Formula 6

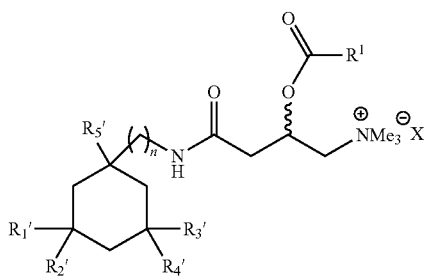

wherein:

Ŕ₁, Ŕ₂, Ŕ₃ and Ŕ₄ are independently H or $C_1$-$C_6$ straight chain or branched alkyls, $C_3$-$C_6$ cycloalkyl, $C_2$-$C_6$ alkenyl, $C_2$-$C_6$ alkynyl; $C_6$-$C_{10}$ aryl unsubstituted or substituted with $C_1$-$C_6$ straight chain or branched alkyl, $C_1$-$C_6$ alkoxyl, 1,3-dioxolanyl, cyano, halo, nitro, trihaloalkyl, $C_1$-$C_6$ acyl, $C_1$-$C_6$ dialkylamino, $C_1$-$C_6$ acylamino, $C_1$-$C_6$ mercaptoalkyl; and alkylaryl ($C_6$-$C_{10}$) or an alkylheteroaryl unsubstituted or substituted with $C_1$-$C_6$ straight chain or branched alkyl, $C_1$-$C_6$ alkoxyl, 1,3-dioxolanyl, cyano, halo, trihaloalkyl, $C_1$-$C_6$ acyl, $C_1$-$C_6$ dialkylamino, and $C_1$-$C_6$ mercaptoalkyl;

Ŕ₁ and Ŕ₂ may be optionally tethered together to form 3- to 7-membered alicyclic ring;

Ŕ₃ and Ŕ₄ may be optionally tethered together to form 3- to 7-membered alicyclic ring;

Ŕ₅ is H or $C_1$-$C_6$ straight chain or branched alkyl;

n=0 or 1; and $R^1$ is independently selected from the group consisting of straight or branched chain $C_1$-$C_6$ alkyl, $C_3$-$C_6$ cycloalkyl; $C_2$-$C_6$ alkenyl; $C_2$-$C_6$ alkynyl; $C_6$-$C_{10}$ aryl unsubstituted or substituted with $C_1$-$C_6$ straight chain or branched alkyl, $C_1$-$C_6$ alkoxyl, 1,3-dioxolanyl, cyano, halo, nitro, trihaloalkyl, $C_1$-$C_6$ acyl, $C_1$-$C_6$ dialkylamino, $C_1$-$C_6$ acylamino, $C_1$-$C_6$ mercaptoalkyl; and alkylaryl ($C_6$-$C_{10}$) or an alkylheteroaryl unsubstituted or substituted with $C_1$-$C_6$ alkyl, $C_1$-$C_6$ alkoxyl, 1,3-dioxolanyl, cyano, halo, trihaloalkyl, $C_1$-$C_6$ acyl, $C_1$-$C_6$ dialkylamino, and $C_1$-$C_6$ mercaptoalkyl, and alkyldiaryls such as diphenylmethyl in which the aryls may be bridged by —CH₂—CH₂— or O or S. The alkyldiaryls may be unsubstituted or substituted with $C_1$-$C_6$ straight chain or branched alkyl, $C_1$-$C_6$ alkoxyl, 1,3-dioxolanyl, cyano, halo, trihaloalkyl, $C_1$-$C_6$ acyl, $C_1$-$C_6$ dialkylamino, and $C_1$-$C_6$ mercaptoalkyl.

Formula 7

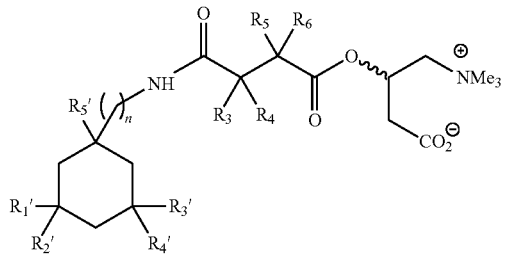

wherein:

Ŕ₁, Ŕ₂, Ŕ₃ and Ŕ₄ are independently H or $C_1$-$C_6$ are straight chain or branched alkyls, $C_3$-C6 cycloalkyl, $C_2$-$C_6$ alkenyl, $C_2$-$C_6$ alkynyl; $C_6$-$C_{10}$ aryl unsubstituted or substituted with $C_1$-$C_6$ alkyl, $C_1$-$C_6$ alkoxyl, 1,3-dioxolanyl, cyano, halo, nitro, trihaloalkyl, $C_1$-$C_6$ acyl, $C_1$-$C_6$ dialkylamino, $C_1$-$C_6$ acylamino, $C_1$-$C_6$ mercaptoalkyl; and alkyl aryl ($C_6$-$C_{10}$) such as benzyl, unsubstituted or substituted with $C_1$-$C_6$ straight chain or branched alkyl, $C_1$-$C_6$ alkoxyl, 1,3-dioxolanyl, cyano, halo, trihaloalkyl, $C_1$-$C_6$ acyl, $C_1$-$C_6$ dialkylamino, and $C_1$-$C_6$ mercaptoalkyl;

Ŕ₁ and Ŕ₂ may be optionally tethered together to form 3- to 7-membered alicyclic ring;

Ŕ₃ and Ŕ₄ may be optionally tethered together to form 3- to 7-membered alicyclic ring;

$R_3$ to $R_6$ are independently selected from the group consisting of hydrogen, hydroxyl, $C_1$-$C_6$ straight chain or branched alkyl; $C_3$-$C_6$ cycloalkyl; $C_6$-$C_{10}$ aryl such as phenyl, naphthyl and the like, unsubstituted or substituted with $C_1$-$C_6$ alkyl, hydroxyl, $C_1$-$C_6$ alkoxyl, 1,3-dioxolanyl, cyano, trihaloalkyl, carboxyl, $C_1$-$C_6$ acyl, $C_1$-$C_6$ hydroxyalkyl, amino, $C_1$-$C_6$ alkylamino, $C_1$-$C_6$ dialkylamino, $C_1$-$C_6$ acylamino, $C_1$-$C_6$ alkylthio, $C_1$-$C_6$ alkoxycarbonyl; and alkylaryl ($C_6$-$C_{10}$) such as benzyl unsubstituted or substituted with $C_1$-$C_6$ alkyl, hydroxyl, $C_1$-$C_6$ alkoxyl, 1,3-dioxolanyl, cyano, trihaloalkyl, carboxyl, $C_1$-$C_6$ acyl, $C_1$-$C_6$ hydroxyalkyl, amino, $C_1$-$C_6$ alkylamino, $C_1$-$C_6$ dialkylamino, $C_1$-$C_6$ alkylthio, $C_1$-$C_6$ alkoxycarbonyl, $C_1$-$C_6$ carboxyalkyl, $C_1$-$C_6$ acylamino, $C_1$-$C_6$ sulfonatoalkyl, $C_1$-$C_6$ sulfamylalkyl, and $C_1$-$C_6$ phosphanatoalkyl;

$R_3$ and $R_4$ may be optionally tethered together to form 3- to 7-membered alicyclic ring;

$R_5$ and $R_6$ may be optionally tethered together to form 3- to 7-membered alicyclic ring;

Ŕ₅ is H or $C_1$-$C_6$ straight chain or branched alkyl;

n=0 or 1; and $X^-$ is a pharmaceutically-acceptable inorganic or organic counter ion.

Formula 8

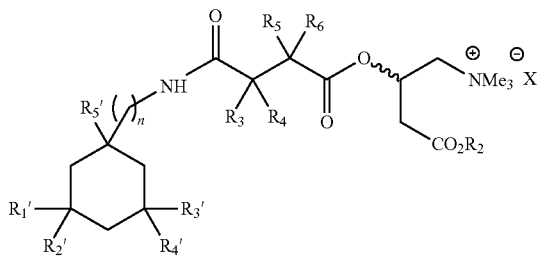

wherein:

$R_1$, $R_2$, $R_3$ and $R_4$ are independently H or $C_1$-$C_6$ straight chain or branched alkyls, $C_3$-$C_6$ cycloalkyl, $C_2$-$C_6$ alkenyl, $C_2$-$C_6$ alkynyl; $C_6$-$C_{10}$ aryl such as phenyl, naphthyl and the like, unsubstituted or substituted with $C_1$-$C_6$ straight chain or branched alkyl, $C_1$-$C_6$ alkoxyl, 1,3-dioxolanyl, cyano, halo, nitro, trihaloalkyl, $C_1$-$C_6$ acyl, $C_1$-$C_6$ dialkylamino, $C_1$-$C_6$ acylamino, $C_1$-$C_6$ mercaptoalkyl; and alkylaryl ($C_6$-$C_{10}$) such as benzyl unsubstituted or substituted with $C_1$-$C_6$ straight chain or branched alkyl, C1-C6 alkoxyl, 1,3-dioxolanyl, cyano, halo, trihaloalkyl, C1-C6 acyl, C1-C6 dialkylamino, and $C_1$-$C_6$ mercaptoalkyl;

$R_1$ and $R_2$ may be optionally tethered together to form 3- to 7-membered alicyclic ring;

$R_3$ and $R_4$ may be optionally tethered together to form 3- to 7-membered alicyclic ring;

$R_3$ to $R_6$ are independently selected from the group consisting of hydrogen, hydroxyl, $C_1$-$C_6$ straight chain or branched alkyl; $C_3$-$C_6$ cycloalkyl; $C_6$-$C_{10}$ aryl unsubstituted or substituted with $C_1$-$C_6$ alkyl, hydroxyl, $C_1$-$C_6$ alkoxyl, 1,3-dioxolanyl, cyano, trihaloalkyl, carboxyl, $C_1$-$C_6$ acyl, $C_1$-$C_6$ hydroxyalkyl, amino, $C_1$-$C_6$ alkylamino, $C_1$-$C_6$ dialkylamino, $C_1$-$C_6$ acylamino, $C_1$-$C_6$ alkylthio, $C_1$-$C_6$ alkoxycarbonyl; and alkylaryl ($C_6$-$C_{10}$) such as benzyl, unsubstituted or substituted with $C_1$-$C_6$ alkyl, hydroxyl, $C_1$-$C_6$ alkoxyl, 1,3-dioxolanyl, cyano, trihaloalkyl, carboxyl, $C_1$-$C_6$ acyl, $C_1$-$C_6$ hydroxyalkyl, amino, $C_1$-$C_6$ alkylamino, $C_1$-$C_6$ dialkylamino, $C_1$-$C_6$ alkylthio, $C_1$-$C_6$ alkoxycarbonyl, $C_1$-$C_6$ carboxyalkyl, $C_1$-$C_6$ acylamino, $C_1$-$C_6$ sulfonatoalkyl, $C_1$-$C_6$ sulfamylalkyl, and $C_1$-$C_6$ phosphanatoalkyl;

$R_3$ and $R_4$ may be optionally tethered together to form 3- to 7-membered alicyclic ring;

$R_5$ and $R_6$ may be optionally tethered together to form 3- to 7-membered alicyclic ring;

$R_5$ is H or $C_1$-$C_6$ straight chain or branched alkyl;

n=0 or 1;

$X^-$ is a pharmaceutically-acceptable inorganic or organic counter ion; and $R^2$ is hydrogen or an easily cleavable group under acidic or neutral conditions such as a t-butyl group or an alkylaryl group such as a benzyl group, wherein the aryl group may be unsubstituted or substituted with $C_1$-$C_6$ straight chain or branched alkyl, $C_3$-$C_6$ cycloalkyl, $C_1$-$C_6$ alkoxyls, 1,3-dioxolanyl, and $C_1$-$C_6$ dialkylamino.

In all the Formulae of this invention, the following terms are to be understood, unless specifically stated otherwise:

Halo, when used alone or as part of a compound or moiety, is to be the ion of chloro, bromo, or iodo.

Alkyl, when used alone or as part of a compound or moiety, is either straight chained or branched when at least 3 carbon atoms or greater and if no number of carbon atoms are specified then it is understood to be from 1 through 4 carbons.

Pharmaceutically-acceptable counter ions, are well known in the art and are discussed in numerous references such as for example *Physicians Desk Reference and Merck Index.*

A preferred embodiment of Formula 1 is represented by Formula 1(A) below,

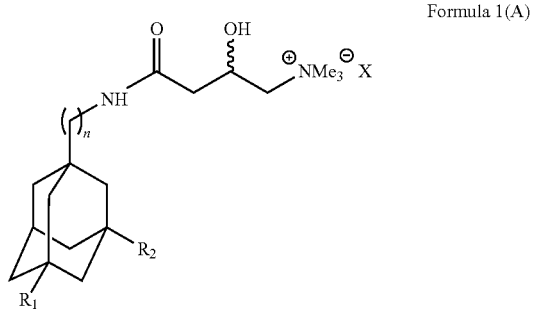

Formula 1(A)

wherein:

$R_1$ and $R_2$ are H or $CH_3$;

n=0, or an integer from 1 through 6; and $X^-$ is any of the pharmaceutically-acceptable counter ions.

These compounds of Formula 1(A) may exist as mixtures of diasteroisomers, if $R_1$ and $R_2$ are different, or when $R_1$ and $R_2$ are the same, as a single stereoisomer, D-(S)— or L-(R)— at the carnitine chiral center, or as a mixture of both isomers. Individual isomers may be prepared starting with chiral starting components or separated from mixtures of isomers by methods well known in the art.

A further preferred embodiment of the compounds of Formula 1 are those shown by Formula 1(B) below,

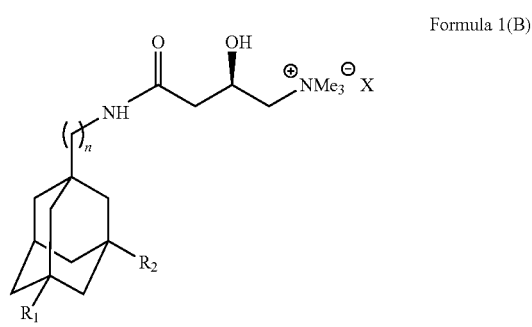

Formula 1(B)

wherein:

$R_1$ and $R_2$ are H or $CH_3$;

n=0 or 1; and $X^-$ is any of the pharmaceutically-acceptable counter ions.

These compounds exist as a single stereoisomer of L-(R)— configuration.

A preferred embodiment of Formula 2 is represented by Formula 2(A) below and its pharmaceutically-acceptable salts,

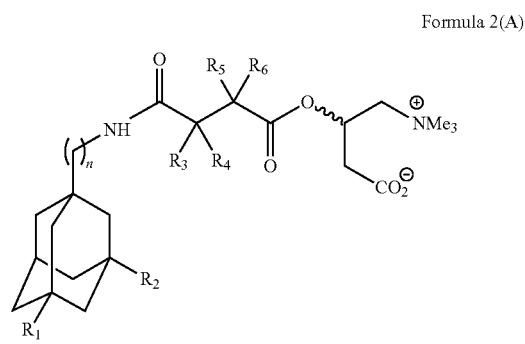

Formula 2(A)

wherein:

$R_1$ and $R_2$ are H and $CH_3$;

n=0 or 1;

$R_3$, $R_4$, $R_5$ and $R_6$ are independently selected to be hydrogen, methyl, ethyl, hydroxyl, alkoxyl, substituted benzoyloxy, or substituted benzyloxy.

The compounds of Formula 2(A) may exist as mixtures of diasteroisomers, if $R_1$, $R_2$ $R_3$, $R_4$, $R_5$ and $R_6$ are different, or when these are the same, as a single stereoisomer, D-(S)— or L-(R)— at the carnitine chiral center, or as a mixture of both isomers. Individual isomers may be prepared starting with chiral starting components or separated from mixtures of isomers by methods well known in the art.

A further preferred embodiment of Formula 2 is represented by Formula 2(B) below and its pharmaceutically-acceptable salts,

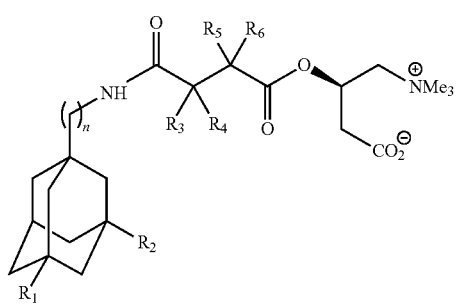

Formula 2(B)

wherein:

$R_1$ and $R_2$ are H or $CH_3$;

n=0 or 1; and $R_3$, $R_4$, $R_5$, $R_6$ are hydrogen.

These compounds of Formula 2(B) exist as a single stereoisomer of L-(R)— configuration.

A preferred embodiment of Formula 3 is represented in Formula 3(A) below and its pharmaceutically-acceptable salts,

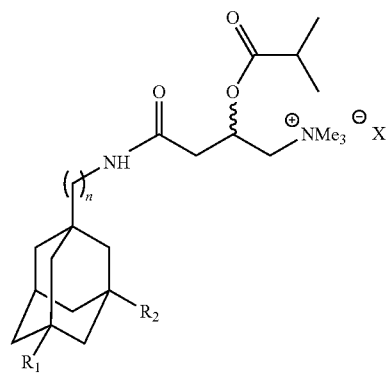

Formula 3(A)

wherein:

$R_1$ and $R_2$ are H or $CH_3$;

n=0 or 1;

$X^-$ is any of the pharmaceutically-acceptable counter ions, and $R^1$ is an isopropyl moiety.

These compounds of Formula 3(A) may exist as a single stereoisomer, D-(S)— or L-(R)—, or as a mixture of both isomers. Individual isomers may be prepared starting with chiral starting components or separated from mixtures of isomers by methods well known in the art.

A further embodiment of compounds of Formula 3 is represented in Formula 3(B) below,

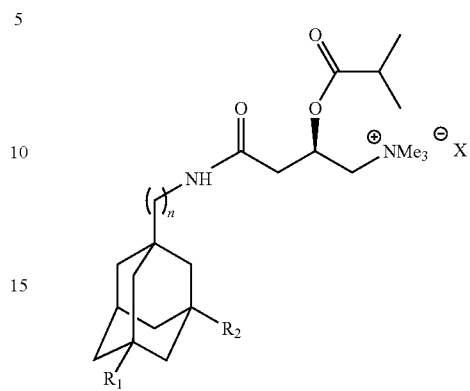

Formula 3(B)

wherein:

$R_1$ and $R_2$ are H or $CH_3$;

n=0 or 1;

$X^-$ is any of the pharmaceutically-acceptable counter ions; and $R^1$ is an isopropyl moiety.

These compounds of Formula 3 B exist as a single stereoisomer of L-(R)— configuration.

A preferred embodiment of Formula 4 is represented by Formula 4(A) below and its pharmaceutically acceptable salts,

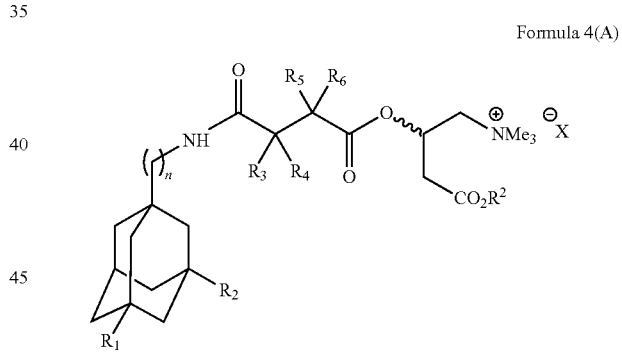

Formula 4(A)

wherein:

$R_1$ and $R_2$ are H or $CH_3$;

n=0 or 1;

$R_3$, $R_4$, $R_5$, $R_6$ are independently selected to be hydrogen, methyl, ethyl, hydroxyl, alkoxyl; and $R^2$ is an easily cleavable group under acidic or neutral conditions such as a t-butyl group or an alkylaryl group wherein the aryl group may be unsubstituted or substituted with straight chain or branched $C_1$-$C_6$ alkyl, $C_3$-$C_6$ cycloalkyl, $C_1$-$C_6$ alkoxyls, 1,3-dioxolanyl, and $C_1$-$C_6$ dialkylamino.

These compounds of Formula 4(A) may exist as mixtures of diastereoisomers.

A further embodiment of Formula 4 is represented by Formula 4(B) below and its pharmaceutically-acceptable salts, Formula 4(B)

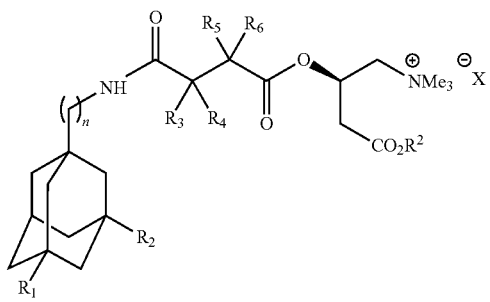

wherein:
$R_1$ and $R_2$ are H or $CH_3$;
n=0 or 1;
$R_3$, $R_4$, $R_5$, $R_6$ are hydrogen; and
$R^2$ is a benzyl group.

These compounds of Formula 4(B) exist as a single stereoisomer of L-(R)— configuration.

A preferred embodiment of Formula 5 is represented by Formula 5(A) below and its pharmaceutically-acceptable salts, Formula 5(A)

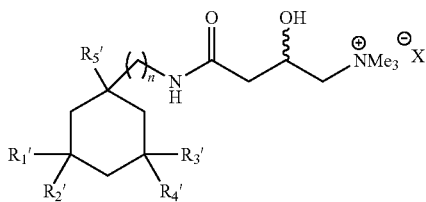

wherein:
$Ŕ_1$, $Ŕ_2$, $Ŕ_3$ and $Ŕ_4$ are independently H or $CH_3$.
$Ŕ_5$ is H or $CH_3$;
n=0 or 1; and
$X^-$ is a pharmaceutically-acceptable inorganic or organic counter ion.

These compounds of Formula 5(A) may exist as mixtures of diastereoisomers. Individual isomers may be prepared starting with chiral starting components or separated from mixtures of isomers by methods well known in the art.

A further embodiment of Formula 5 is represented by Formula 5(B) below and its pharmaceutically-acceptable salts, Formula 5(B)

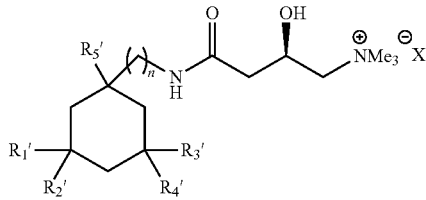

wherein:
$Ŕ_1$, $Ŕ_2$, $Ŕ_3$, $Ŕ_4$ and $Ŕ_5$ are H or $CH_3$;
n=0 or 1; and
$X^-$ is a pharmaceutically acceptable inorganic or organic counter ion.

These compounds of Formula 5(B) exist as a single stereoisomer of L-(R)— configuration.

A preferred embodiment of Formula 6 is represented by Formula 6(A) below and its pharmaceutically-acceptable salts, Formula 6(A)

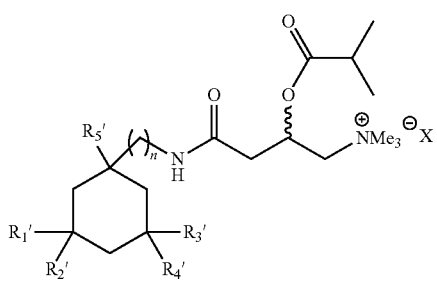

wherein:
$Ŕ_1$, $Ŕ_2$, $Ŕ_3$, $Ŕ_4$ are independently H or $CH_3$;
$Ŕ_5$ is H or $CH_3$;
n=0 or 1;
$R^1$ is an isopropyl moiety; and
$X^-$ is a pharmaceutically-acceptable inorganic or organic counter ion.

These compounds of Formula 6(A) may exist as mixtures of diastereoisomers.

A preferred embodiment of Formula 6 is represented by Formula 6(B) below and its pharmaceutically-acceptable salts, Formula 6(B)

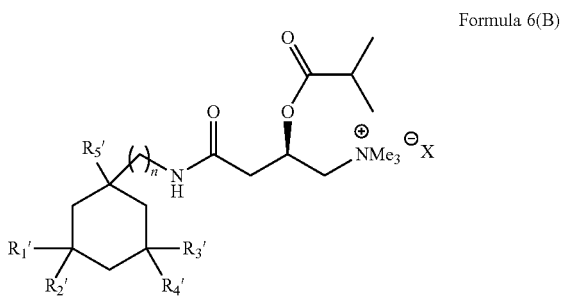

wherein:
$Ŕ_1$, $Ŕ_2$, $Ŕ_3$, $Ŕ_4$ and $Ŕ_5$ are H or $CH_3$;
$R^1$ is an isopropyl moiety;
n=0 or 1; and
$X^-$ is a pharmaceutically-acceptable inorganic or organic counter ion.

These compounds of Formula 6(B) exist as a single stereoisomer of L-(R)— configuration.

A preferred embodiment of Formula 7 is represented by Formula 7(A) below and its pharmaceutically-acceptable salts, Formula 7(A)

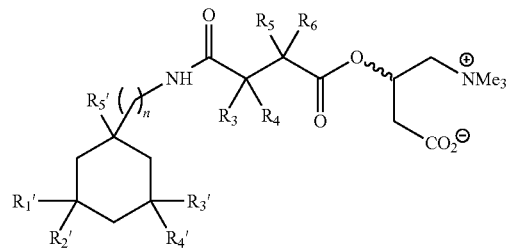

wherein:
Ŕ$_1$, Ŕ$_2$, Ŕ$_3$, Ŕ$_4$ are independently H or CH$_3$;
Ŕ$_5$ is H or CH$_3$;
n=0 or 1; and
R$_3$, R$_4$, R$_5$, and R$_6$ are independently selected to be hydrogen, methyl, ethyl, hydroxyl, alkoxyl.

These compounds of Formula 7(A) may exist as mixtures of diastereoisomers.

A further embodiment of Formula 7 is represented by Formula 7(B) below and its pharmaceutically-acceptable salts,

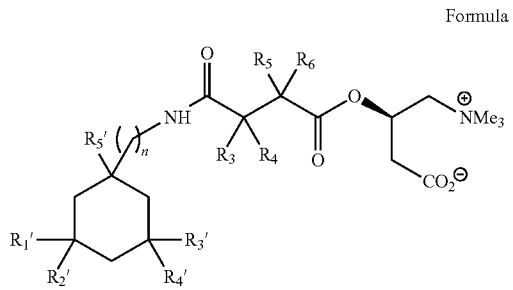

Formula 7(B)

wherein:
Ŕ$_1$, Ŕ$_2$, Ŕ$_3$, Ŕ$_4$ and Ŕ$_5$ are H or CH$_3$;
n=0 or 1;
X$^-$ is a pharmaceutically-acceptable inorganic or organic counter ion; and
R$_3$, R$_4$, R$_5$ and R$_6$ are hydrogen.

These compounds of Formula 7(B) exist as a single stereoisomer of L-(R)— configuration.

A preferred embodiment of Formula 8 is represented by Formula 8(A) below and its pharmaceutically-acceptable salts,

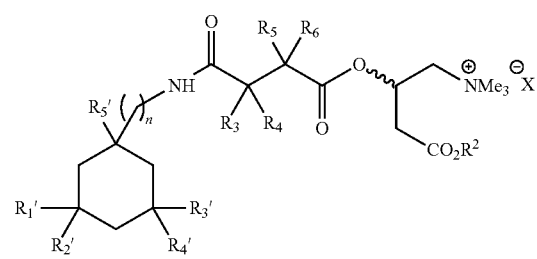

Formula 8(A)

wherein:
Ŕ$_1$, Ŕ$_2$, Ŕ$_3$ and Ŕ$_4$ are independently H or CH$_3$;
Ŕ$_5$ is H or CH$_3$;
n=0 or 1;
X$^-$ is a pharmaceutically-acceptable inorganic or organic counter ion;
R$_3$, R$_4$, R$_5$ and R$_6$ are independently selected to be hydrogen, methyl, ethyl, hydroxyl, alkoxyl; and
R$^2$ is hydrogen or an easily cleavable group under acidic or neutral conditions such as a t-butyl group or an alkylaryl group such as a benzyl group wherein the aryl group may be unsubstituted or substituted with straight chain or branched C$_1$-C$_6$ alkyl, C$_3$-C$_6$ cycloalkyl, C$_1$-C$_6$ alkoxyls, 1,3-dioxolanyl, and C$_1$-C$_6$ dialkylamino.

These compounds of Formula 8(A) may exist as mixtures of diastereoisomers.

A further embodiment of Formula 8 is represented by Formula 8(B) below and its pharmaceutically-acceptable salts,

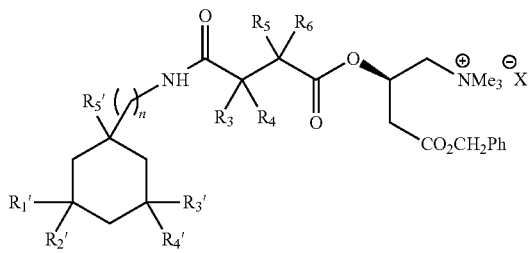

Formula 8(B)

wherein:
Ŕ$_1$, Ŕ$_2$, Ŕ$_3$, Ŕ$_4$ and Ŕ$_5$ are H or CH$_3$;
n=0 or 1;
X$^-$ is a pharmaceutically-acceptable inorganic or organic counter ion;
R$_3$, R$_4$, R$_5$ and R$_6$ are hydrogen; and
R$^2$ is a benzyl group.

These compounds of Formula 8(B) exist as a single stereoisomer of L-(R)— configuration.

Pharmacology

Compounds 3-(3,5-dimethyladamantan-1-ylcarbamoyl)-(R)-2-hydroxypropyl)-trimethyl ammonium chloride [Formula 1(B); R$_1$ and R$_2$ are CH$_3$; n=0], and 3-benzyloxycarbonyl-(R)-2-{[(3,5-dimethyladamantan-1-ylcarbamoyl)-propionyloxy]propyl}-trimethyl ammonium bromide [Formula 4(B); R$_1$ and R$_2$ are CH$_3$; n=0; R$_3$, R$_4$, R$_5$, R$_6$ are hydrogen; and R$^2$ is a benzyl group] were selected for in vivo testing in mice, since both are potential prodrugs for memantine and L-carnitine through in vivo enzymatic hydrolysis of either an amide or ester linkages. Since memantine has N-methyl-D-aspartate (NMDA) antagonist properties, it was assumed that the above compounds would share these properties and therefore a test was utilized that identifies NMDA antagonist activity in vivo. Briefly, this test measures seizure activity and lethality in mice produced by the administration of NMDA antagonists which block these parameters in a dose-dependent manner (see Leander, J. D., et al., *Brain Res.* 448, 115-120 (1988), N-methyl-D-aspartate acid-induced lethality in mice: selective antagonism by phencyclidine-like drugs; Parsons, C. G., et al., *Neuropharmacol.* 34, 1239-1258 (1995).

Test protocol: Male, NIH-Swiss mice weighing 25-30 grams were pretreated with either compound by the subcutaneous (SC) route of administration and 30 minutes later NMDA (200 mg/kg) was administered intraperitoneally (IP) Animals were observed for 30 minutes and the number of seizure episodes, and whether death occurred was recorded, as well as the time to produce each seizure event and the time of death. Memantine (30 mg/kg; SC) was used as a positive control in each experiment and there were n=8 mice/group for all conditions.

Results: 3-(3,5-dimethyladamantan-1-ylcarbamoyl)-(R)-2-hydroxypropyl)-trimethyl ammonium chloride slightly increased the time to lethality following the SC administration of 120 mg/kg; however, toxicity (e.g. tremors, lethality in n=3 mice) was observed at this dose. A dose of 60 mg/kg (SC) was inactive. 3-benzyloxycarbonyl-(R)-2-{[3,5-dimethyladamantan-1-ylcarbamoyl)-propionyloxy]propyl}-trimethyl ammonium bromide at a dose of 90 mg/kg (SC) markedly increased the time to produce clonic seizures and death. These results are suggestive of NMDA antagonist activity.

Pharmaceutical Compositions:

The pharmaceutical composition may also contain physiologically tolerable diluents, carriers, adjuvants, and the like. The phrase "pharmaceutically-acceptable" means those formulations which are, within the scope of sound medical judgment, suitable for use in contact with the tissues of humans and animals without undue toxicity, irritation, allergic response and the like, and are commensurate with a reasonable benefit/risk ratio. Pharmaceutically-acceptable salts are well-known in the art, and are described by Berge et al., *J. Pharm. Sci.* 66, 1-16 (1977), incorporated herein by reference. Representative salts include, but are not limited to, acetate, adipate, alginate, citrate, aspartate, benzoate, benzenesulfonate, chloride, bromide, bisulfate, butyrate, camphorate, camphor sulfonate, gluconate, glycerophosphate, hemisulfate, heptanoate, hexanoate, fumarate, maleate, succinate, oxalate, citrate, hydrochloride, hydrobromide, hydroiodide, lactate, maleate, nicotinate, 2-hydroxyethansulfonate (isothionate), methane sulfonate, 2-naphthalene sulfonate, oxalate, palmitoate, pectinate, persulfate, 3-phenylpropionate, picrate, pivalate, propionate, tartrate, phosphate, glutamate, bicarbonate, p-toluenesulfonate, undecanoate, lithium, sodium, potassium, calcium, magnesium, aluminum, ammonium, tetramethyl ammonium, tetraethylammonium, methylammonium, dimethylammonium, trimethylammonium, triethylammonium, diethylammonium, and ethylammonium, and the like.

The pharmaceutical compositions of this invention can be administered to humans and other mammals enterally or parenterally in a solid, liquid, or vapor form. Parenteral route includes intravenous, intramuscular, intraperitoneal, intrasternal, and subcutaneous injection or infusion. The compositions can also be delivered through a catheter for local delivery at a target site, via an intracoronary stent (a tubular device composed of a fine wire mesh), or via a biodegradable polymer.

The active compound is mixed under sterile conditions with a pharmaceutically acceptable carrier along with any needed preservatives, excipients, buffers, or propellants. Ophthalmic formulations, eye ointments, powders and solutions are also contemplated as being within the scope of this invention.

Actual dosage levels of the active ingredients in the pharmaceutical formulation can be varied so as to achieve the desired therapeutic response for a particular patient. The selected dosage level will depend upon the activity of the particular compound, the route of administration, the severity of the condition being treated, and prior medical history of the patient being treated. This evaluation of dose is well within the ability of the medical staff to determine.

The phrase "therapeutically effective amount" of the compound of the invention means a sufficient amount of the compound to treat disorders, at a reasonable benefit/risk ratio applicable to medical treatment. It will be understood, however, that the total daily usage of the compounds and compositions of the present invention shown by Formula (I) will be decided based on clinical experience. The specific therapeutically effective dose level for any particular patient will depend upon a variety of factors including the disorder being treated, the severity of the disorder; activity of the specific compound employed; the number of doses administered in a specified time; the specific composition employed; age, body weight, general health, sex, diet of the patient; the time of administration, route of administration, and rate of excretion of the specific compound employed; and the duration of the treatment. The compounds of the present invention may also be administered in combination with other drugs, if medically necessary, to treat the disorder concerned.

Compositions suitable for parenteral injection may comprise physiologically acceptable, sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethyleneglycol, glycerol, and the like), vegetable oils (such as olive oil), injectable organic esters such as ethyl oleate, and suitable mixtures thereof. These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like.

Suspensions, in addition to the active compounds, may contain suspending agents, as for example, ethoxylated isostearyl alcohols, polyoxyethylene sorbitan esters, microcrystalline cellulose, aluminum metahydroxide, bentonite, agar-agar and tragacanth, or mixtures of these substances, and the like. Prolonged absorption of the injectable pharmaceutical form can be brought about by the use of agents delaying absorption, for example, aluminum monostearate and gelatin. Proper fluidity can be maintained, for example, by the use of coating materials such as lecithin, by the maintenance of the required particle size in the case of dispersions, and by the use of surfactants. In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending on the ratio of drug to polymer and the nature of the particular polymer employed, the rate of the drug release can be controlled. Examples of other biodegradable polymers include poly(orthoesters) and poly(anhydrides). Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Dosage forms for topical administration include powders, sprays, ointments, patch and inhalants. Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol, and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally in a delayed manner. Examples of embedding compositions which can be used include polymeric substances and waxes. The active compounds can also be in micro-encapsulated form, if appropriate, with one of more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof. Besides inert diluents, the oral suspending agents, sweetening, flavoring perfuming agents.

Compositions for rectal or vaginal administration are preferably suppositories which can be prepared by mixing the compounds of this invention with suitable non-irritating excipients or carriers such as cocoa butter, polyethylene glycol or a suppository wax which are solid are room temperature but liquid at body temperature and therefore melt in the rectum or vaginal cavity and release the active compound.

The present invention also provides pharmaceutical compositions that comprise compounds of the present invention formulated together with one or more non-toxic pharmaceutically acceptable carriers. Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present invention compositions in liposome form can contain, in addition to a compound of the present invention, stabilizers, preservatives, excipients and the like. The preferred lipids are natural and synthetic phospholipids and phosphatidyl cholines (lecithins) used separately or together. Methods to form liposomes are known in the art [e.g., Liposomes in Biomedical Applications: Drug targeting and delivery, Vol. 6, by P. N. Shek, pub. CRC (Aug. 3, 1995)].

The examples which follow are presented to describe preferred embodiments and utilities of the invention and are not meant to limit the invention. The description is intended as a non-limiting illustration, since many variations will become apparent to those skilled in the art in view thereof. It is intended that all such variations are within the scope and spirit of the appended claims. Changes can be made in the composition, operation, and arrangement of the method of the present invention described herein without departing from the concept and scope of the invention.

Processes to Prepare the Compounds of Formula (I)

Synthesis of the Compounds of Formula (I), Specifically Formulae 1-4

Scheme 1:

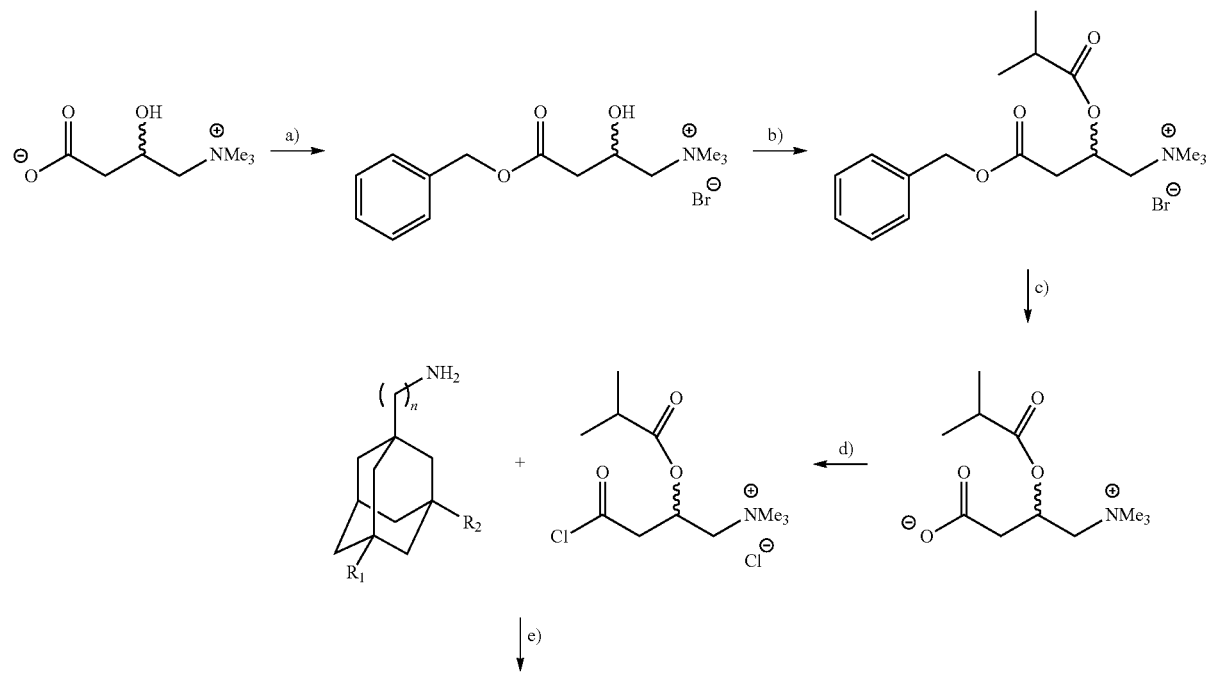

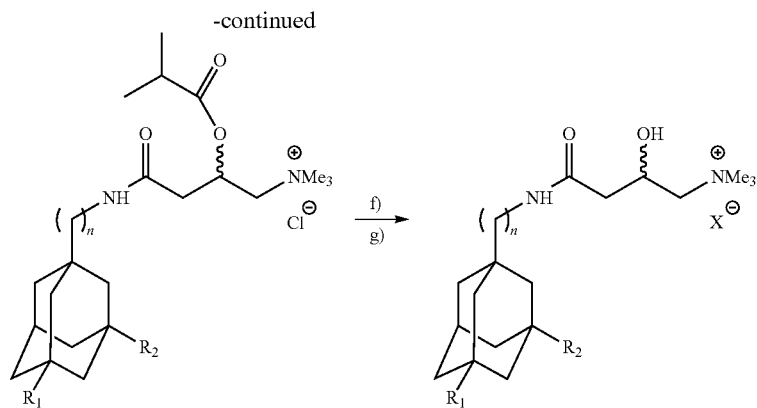

a) benzyl bromide, 125° C., DMF
b) isobutyric anhydride, pyridine;
c) H$_2$, 10% Pd/C, ethanol;
d) oxalyl chloride;
e) pyridine, dichloromethane;
f) methanol, K$_2$CO$_3$;
g) H$^+$X$^-$.

By a similar sequence of steps, compounds of Formula (I), specifically Formulae 5 and 6 may be prepared e) pyridine, dichloromethane;
h) EDC or DCC [Nakaya, K-I, et al., *Bull. Chem. Soc. Jpn.* 74, 173-178 (2001)]
c) H$_2$, 10% Pd/C;

By a similar sequence of steps, compounds or Formula (I), specifically Formula 7 and 8 may be prepared

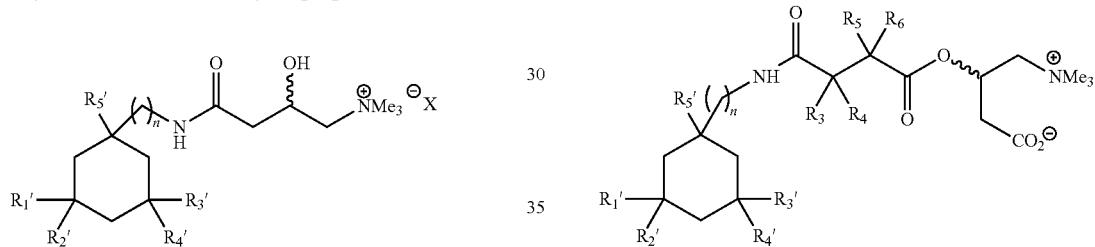

Scheme 2:

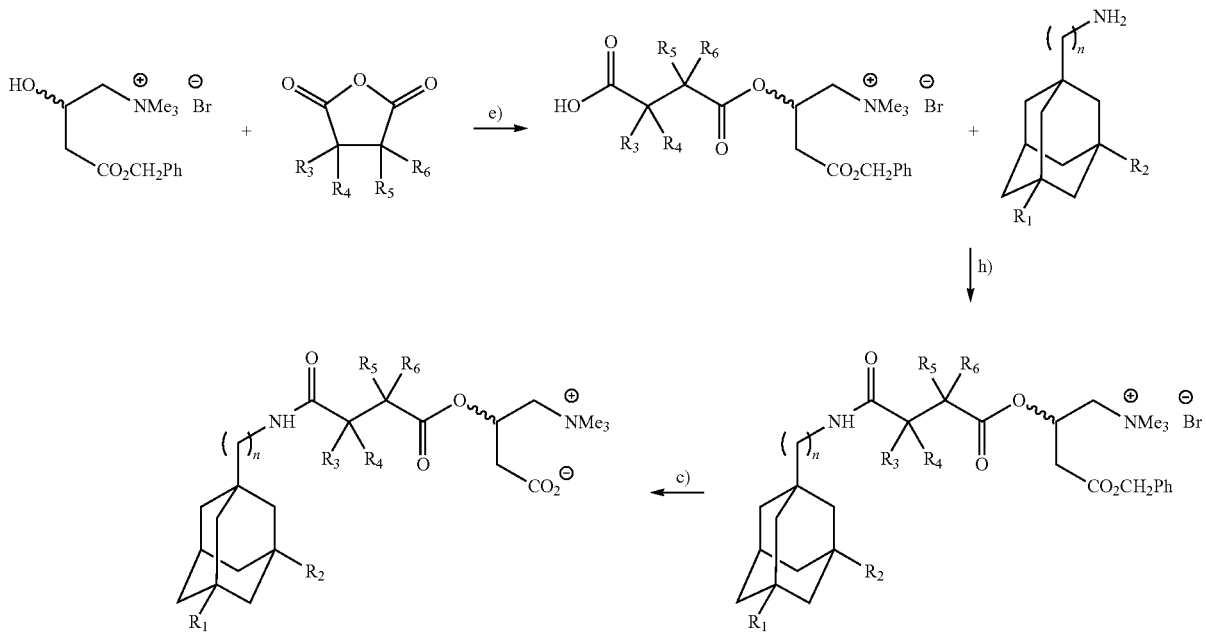

Scheme 3:

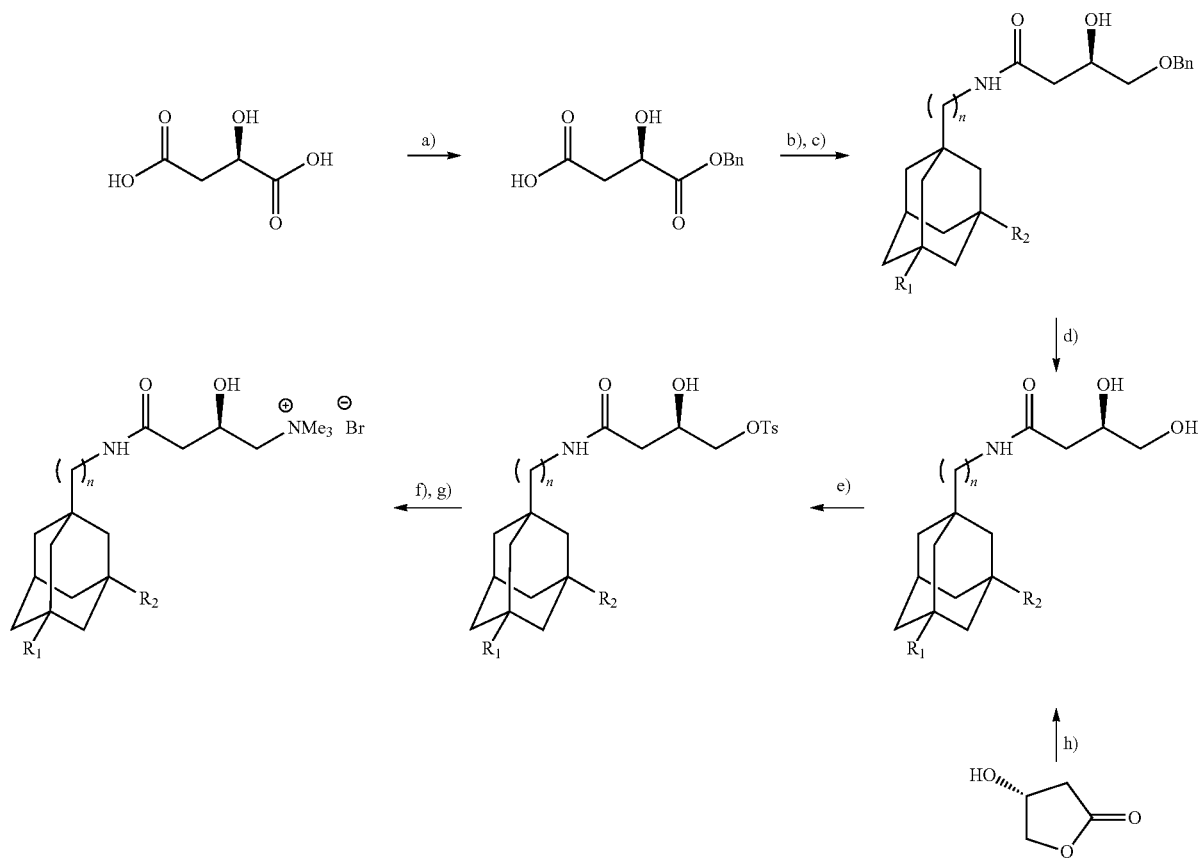

a) TFA, BnOH, 84%; [Bergeron, R. J., et al., *Tetrahedron: Asym.* 10, 4285-4294 (1999)]

b) N-hydroxysuccinimide, DCC/THF; [Bergeron, R. J., et al., *Tetrahedron: Asym.* 10, 4285-4294 (1999)]

c) memantines:

d) LiBH$_4$/THF; [Kanatomo, K. et al., *Chem. Pharm. Bull.* 32, 4625-4631 (1984)]

e) TsCl, pyr.; [Bellamy, F. D., et al., *Tetrahedron Lett.* 31, 7323-7326 (1990)]

f) N(CH$_3$)$_3$, toluene;

g) ion-exchange chromatography h) memantines, THF/Δ [Huang, G. et al., *Tetrahedron* 54, 1355-1360 (1998); Zang, J. et al., *J. Carbohydr. Chem.* 17, 341-358 (1998)]

By a similar sequence of steps, compounds of Formula (I), specifically Formula 5 may be prepared Scheme 4:

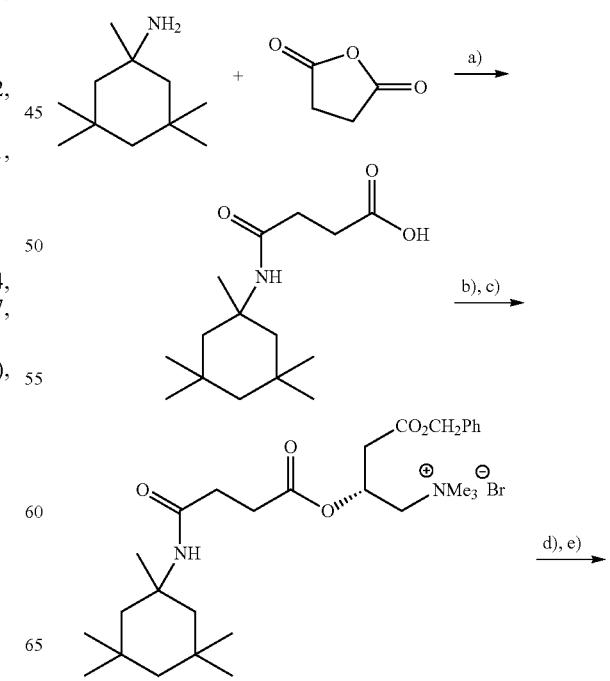

-continued

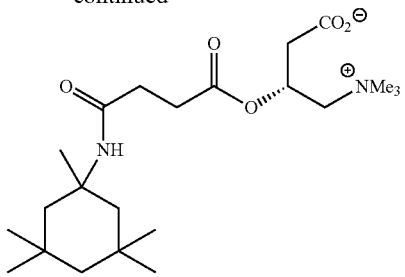

a) pyr., 80%;
b) SOCl$_2$;
c) L-carnitine benzyl ester/CH$_3$CN, Δ
d) H$_2$, Pd/C, THF/CH$_3$OH;
e) RP chromatography Scheme 5:
Synthesis of 1,1,3,3,5-pentamethylcyclohexanamine (neramexane)

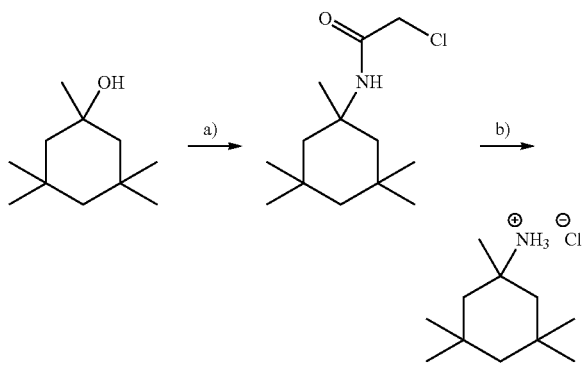

a) NCCH$_2$Cl, H$_2$SO$_4$/AcOH, 86%; [Jirgensons, A. et al., *Synthesis* 12, 1709-1712 (2000); Jirgensons, A., et al., *Eur. J. Chem.* 35, 555-565 (2000); Gold, M. et al., U.S. Pat. No. 6,034,134]
b) thiourea, AcOH/EtOH, 89%

The synthesis of representative conjugates 1-4 of L-carnitine with memantine and neramexane are shown in Schemes 6-9. In general, the succinate ester and isobutyrate ester of L-carnitine were prepared and coupled with both neramexane (Jirgenson, A, et al., *Synthesis* 12, 1709-1712 (2002), and U.S. Pat. No. 6,034,134) and commercially available memantine (Acros). Unlike in the previous literature preparations of the succinate ester (see Johnson, D. W., *Chem. Phys. Lipids* 129(2), 161-172 (2004), and isobutyrate ester of L-carnitine (Gaskell, S. J., et al., *Anal. Chemistry* 58(13), 2801-2805 (1986); Cipollone, M., et al., *J. Med. Chem.* 35, 903-911 (2000), L-carnitine was first protected as the benzyl ester. The benzyl ester of L-carnitine (1-04) was treated with an excess of either succinic anhydride or isobutyric anhydride in the presence of pyridine. After purification by column chromatography, the succinate ester of carnitine benzyl ester was coupled with either neramexane (3-01) or memantine (4-01) with the use of DCC. The succinate-bridged compounds were then purified by column chromatography until pure by NMR. The isobutyrate ester of L-carnitine benzyl ester (1-03) was hydrogenated to remove the protective benzyl ester. The free acid (1-02) was coupled to either neramexane or memantine using DCC. Finally, the protective isobutyrate esters were removed with potassium carbonate (in methanol) to generate the L-carnitine amide with neramexane (1) or memantine (2). Both amides were purified by column chromatography until pure by NMR. Once pure, all four compounds were freeze-dried under high vacuum at room temperature until a constant weight was achieved. A portion of the dried compounds was analyzed by NMR, optical rotation, HPLC, HRMS, and CHN.

Determination of Stereochemical Purity

In order to verify that the carnitine present in 1 and 2 maintained the R— configuration, several attempts were made to prepare the (R)- and (S)-Mosher's esters of the products. It was clear from the experiments that the Mosher' esters were not stable in the presence of base and rapidly eliminated methoxy-(trifluoromethyl)phenyl acetic acid after the ester formed. This was not completely unexpected. Both the final precursors (1-01 and 2-01) eliminated isobutyric acid in the presence of base.

In order to determine the stereochemical purity of 3-01 and 4-01, the material was hydrogenated to remove the benzyl ester, complexed with mucic acid (see U.S. Pat. No. 5,952, 379), to improve stability, and compared by chiral HPLC to standards prepared in the same fashion from (S)-carnitine. The HPLC data indicated that less than 1% of the S-isomer was present in 3 and 4. Since all compounds were produced under similar conditions, it is likely that 1 and 2 maintained their stereochemical purity as well.

Scheme 6:
Synthesis of the L-carnitine conjugates of neramexane

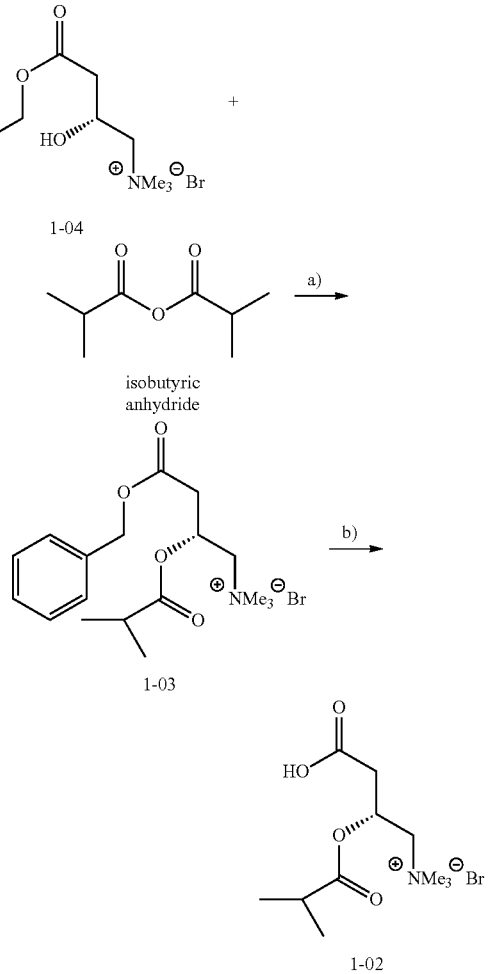

-continued

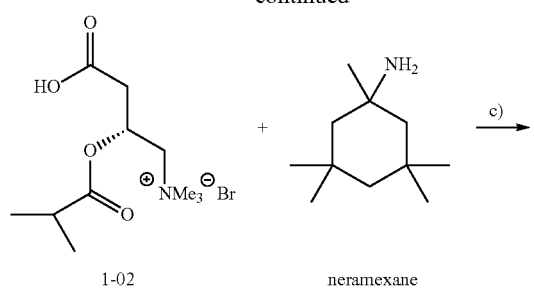

1-02    neramexane

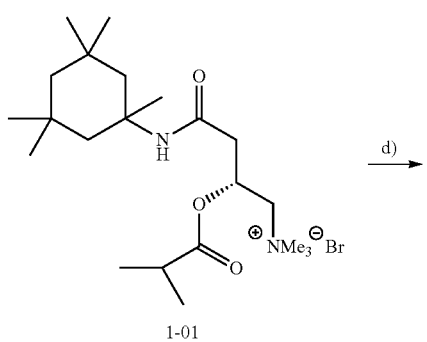

1-01

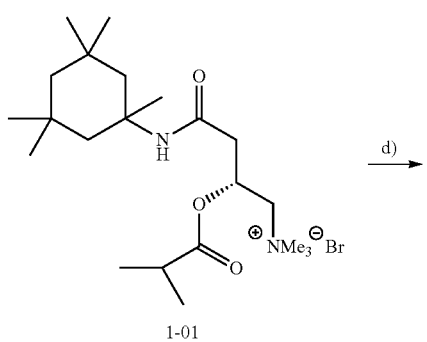

1 a) pyridine, room temperature;
b) H$_2$, 10% Pd/C;
c) DCC, CH$_2$Cl$_2$;
d) potassium carbonate, methanol, hydrochloric acid.

Scheme 7:
Synthesis of the L-carnitine conjugates of memantine

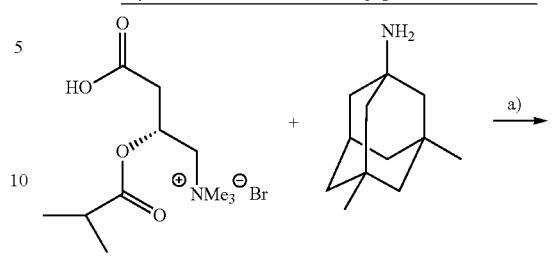

1-02    memantine

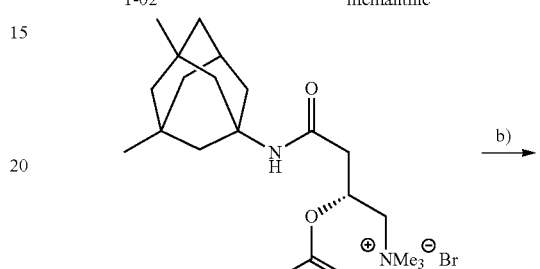

2-01

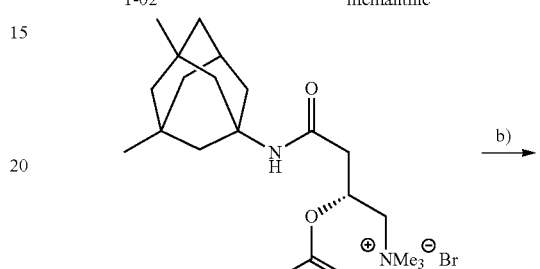

2 a) DCC, CH$_2$Cl$_2$;
b) potassium carbonate, methanol, hydrochloric acid.

Scheme 8:
Synthesis of the neramexane derivatives with succinyl linker

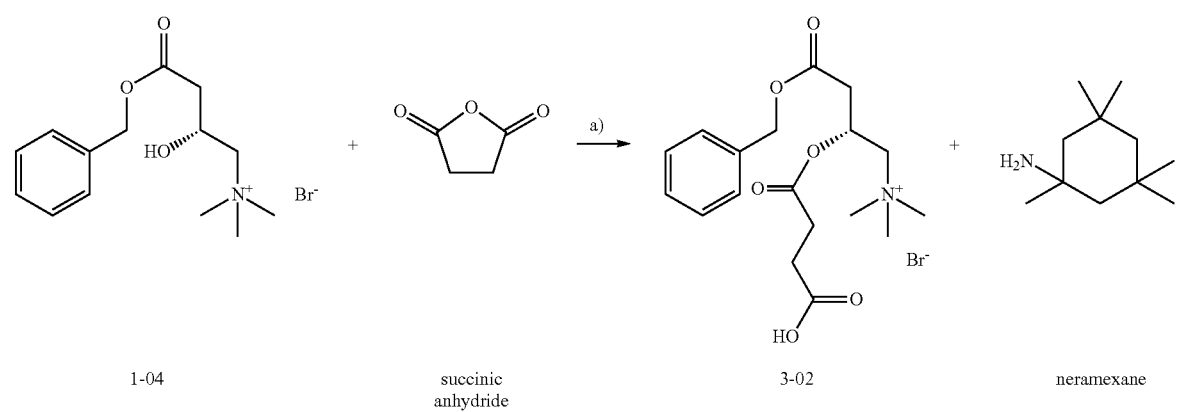

1-04    succinic anhydride    3-02    neramexane b)

-continued

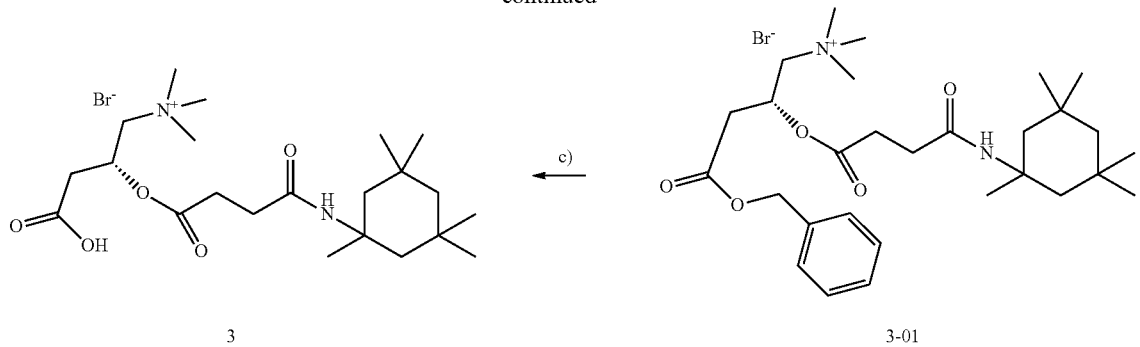

a) pyridine, room temperature;
b) DCC, CH$_2$Cl$_2$;
c) H$_2$, 10% Pd/C.

Scheme 9:
Synthesis of the memantine derivatives with succinyl linker

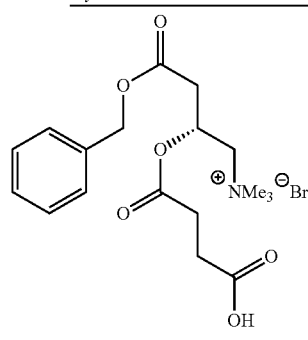

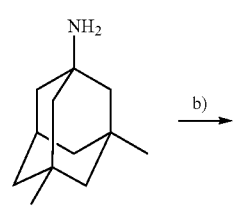

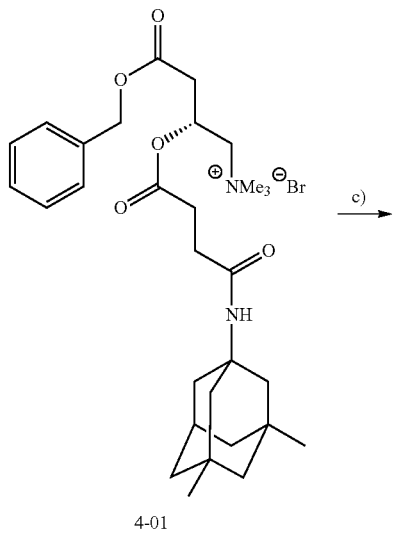

-continued b) DCC, CH$_2$Cl$_2$;
c) H$_2$, 10% Pd/C.

For the following examples the various equipment and methods were used to run the various described tests for the results reported in the examples below.

EXAMPLES

General Procedures

The synthesis of compounds 1, 2, 3-01 and 4-01 was carried out in several batches (0.3-10.0 g). Reagents were purchased at the highest obtainable purity from Lancaster, Sigma-Aldrich, or Acros, except for solvents, which were purchased from either Fisher Scientific or Mallinckrodt.

High-resolution mass spectra were obtained from the Chemistry Department at the University of Florida. The combustion (CHN) analysis for the final compounds was done at Atlantic Microlab (Norcross, Ga. 30091). The NMR and high-resolution mass spectra obtained for the final compounds are consistent with the proposed structures. Each final compound had a small negative optical rotation as expected. Some problems were observed with the HPLC data. The impurities tended to be better chromophores than the desired products, leading to HPLC data that were not consistent with the NMR data. Also, suitable HPLC conditions could not be found for 3-01 and 4-01, using a series of columns and conditions. A portion of the material did not adhere to the column and the remainder came off as a series of peaks. This behavior was also seen during column chromatography, and was more pronounced when a gradient system was used. Finally, the CHN analysis for each compound did not match the calculated value, primarily due to hygroscopicity of the samples. Each compound appears to contain 1.5-3 equivalents of water. In the case of 1 and 2, dichloromethane was used to prepare the CHN samples (in order to drive off some of the water). Unfortunately, additional drying at Atlantic Microlab failed to remove all of the dichloromethane, leading to the high chlorine levels found for those compounds.

The invention will be further clarified by a consideration of the following examples, which are intended to be purely exemplary of the present invention.

Example 1

1: [(R)-2-Hydroxy-3-(1,3,3,5,5-pentamethyl-cyclohexylcarbamoyl)-propyl]-trimethylammonium chloride Isobutyric ester of L-carnitine benzyl ester: 1-03

A mixture of the benzyl ester of L-carnitine bromide (1-04, 10.0 g, 0.030 mol), isobutyric anhydride (20.0 g, 0.126 mol), pyridine (10 mL), and dichloromethane (10 mL) was stirred at room temperature for 20 hours under an argon atmosphere. After 20 hours, toluene (200 mL) was added and the precipitate was filtered. The precipitate was stirred with diethyl ether (100 mL) at room temperature for 1 hour under an argon atmosphere. The precipitate was filtered a second time and dried under high vacuum at room temperature until the weight was constant. The experiment produced the isobutyric ester of L-carnitine benzyl ester (1-03, 11.01 g, 90.9% yield) as a light brown, wax-like solid. Its spectra are:

$^1$H NMR (300 MHz, DMSO): δ 7.39 (5H, m), 5.52 (1H, m), 5.13 (2H, s), 3.92-3.76 (2H, m), 3.15 (9H s), 2.87 (2H, dd, J=6.6, 6.3 Hz), 2.50 (1H, m), 1.04 (3H, d, J=7.5 Hz), 1.02 (3H, d, J=7.8 Hz); and $^{13}$C NMR (75 MHz, DMSO): δ 174.84, 168.62, 135.45, 128.28, 128.04, 66.87, 66.04, 64.64, 52.59, 37.08, 18.39, 18.23.

Isobutyric ester of L-carnitine: 1-02

The benzyl protected isobutyric ester of L-carnitine (1-03, 10.60 g, 0.026 mol) was dissolved in ethanol (100 mL) and added to 10% palladium-on-carbon (2.0 g). The mixture was hydrogenated in a small Parr apparatus for 6 hours at room temperature under 42 psi hydrogen. The mixture was filtered through a pad of Celite 521 (20 g) and concentrated under reduced pressure. The remaining solid was dried at room temperature under high vacuum until the product weight was constant (6 hours). The experiment produced the isobutyric ester of L-carnitine (1-02, 6.8 g, 82% yield) as an off-white, wax-like solid. Its spectra are:

$^1$H NMR (300 MHz, CD$_3$OD): δ 6.62 (m, 1H), 3.93 (dd, 1H, J=14.4, 8.7 Hz), 3.75 (d, 1H, J=14.4 Hz), 3.24 (s, 9H), 2.77 (d, 2H, J=5.7 Hz), 2.60 (m, 1H), 1.18 (d, 6H, J=6.9 Hz); and $^{13}$C NMR (75 MHz, CD$_3$OD): δ 177.19, 172.30, 69.53, 66.31, 54.70, 38.00, 35.35, 19.32, 19.05.

A mixture of the isobutyric ester of L-carnitine benzyl ester (1.94 g, 6.21 mmol), neramexane (0.95 g, 5.61 mmol), and N,N'-dicyclohexylcarbodiimide (DCC, 1.20 g, 5.81 mmol) in dichloromethane (10 mL) was stirred at room temperature for 2 hours under an argon atmosphere. The precipitated DCU was removed by filtration, and the dichloromethane solution was directly purified by column chromatography on silica gel (25 g) eluting with 15% methanol in dichloromethane. The product containing fractions were combined and concentrated under reduced pressure. The remaining gel was dried under high vacuum at room temperature until the weight was constant. The experiment produced 1-01 as a light yellow gel (0.50 g, 19% yield). Its spectra are:

$^1$H NMR (300 MHz, CD$_3$OD): δ 7.16 (s, 1H), 5.57 (m, 1H), 3.82 (dd, 1H, J=14.1, 8.1 Hz), 3.65 (d, 1H, J=14.1 Hz), 3.15 (s, 9H), 2.53 (m, 3H), 2.16 (d, 2H, J=14.4 Hz), 1.26-1.21 (m, 4H), 1.11 (s, 3H), 1.04-0.96 (m, 9H), 0.83 (br s, 6H); and $^{13}$C NMR (75 MHz, CD$_3$OD): δ 177.13, 170.15, 69.91, 66.72, 56.06, 54.98, 54.73, 52.82, 50.00, 40.70, 36.48, 35.30, 32.44, 30.77, 29.03, 28.96, 19.25, 19.16.

The isobutyric ester (1-01, 0.50 g, 1.07 mmol) was dissolved in anhydrous methanol (10 mL). Dry potassium carbonate (1.0 g, 7.23 mmol) was added and the mixture was vigorously stirred for 5 hours at room temperature under an argon atmosphere. The excess potassium carbonate was removed by filtration and the methanol solution was acidified with concentrated hydrochloric acid (1.0 mL) in methanol (20 mL). The methanol was concentrated under reduced pressure and the residual gel was dissolved in a small volume of DIUF water (5 mL) and purified on ODS-silica gel (20 g), eluting with 50% methanol in dilute hydrochloric acid (0.05%).

The product containing fractions were combined and the volume was reduced by 50% under reduced pressure. The remaining aqueous portion was freeze-dried until a constant weight was achieved. The experiment generated 1 (0.32 g, 80% yield) as a colorless foam. Its spectra are:

$^1$H NMR (300 MHz, DMSO-d$_6$): δ 7.16 (s, 1H), 4.37 (m, 1H), 3.34 (m, 2H), 3.14 (s, 9H), 2.34-2.15 (m, 4H), 1.24 (m, 1H), 1.20 (s, 3H), 1.05 (s, 6H), 1.02-0.91 (m, 3H), 0.83 (s, 6H);

$^{13}$C NMR (75 MHz, DMSO-d$_6$): δ 169.42, 69.65, 62.71, 53.59, 53.41, 51.40, 46.69, 46.52, 42.25, 35.85, 31.07, 30.03, 28.08, 28.03;

HPLC analysis: 35% ACN/65% phosphate buffer (25 mmol, pH=2.5), Gemini C18, 5µ, 4.6×250 mm (serial #262049-2), 40 C, 1 mL/min room temperature=8.363 min, purity=91.4% (at 205 nm);

HRMS: LSIMS (FAB) [M-Cl$^-$]$^+$; theoretical 313.2850. found 313.2845;

Specific rotation: [α]$_D^{25}$=−8.08 deg (25° C., c=0.00321 g×mL$^{-1}$, ethanol, 589 nm); and CHN analysis:
found: C, 55.34; H, 10.43; N, 6.83; Cl, 12.51.
calculated: C, 61.96; H, 10.69; N, 8.03; Cl, 10.16 (C$_{18}$H$_{37}$ClN$_2$O$_2$).
best fit: C, 55.50; H, 10.43; N, 7.13; Cl, 12.02 (C$_{18}$H$_{37}$ClN$_2$O$_2$+1.66H$_2$O+0.16CH$_2$Cl$_2$, CH$_2$Cl$_2$ used in sample transfer, not present in original sample).

Example 2

2: [3-(3,5-Dimethyl-adamantan-1-ylcarbamoyl)-(R)-2-hydroxy-propyl]-trimethylammonium chloride A mixture of the isobutyric ester of L-carnitine (1-02, 0.97 g, 3.10 mmol), memantine (0.50 g, 2.78 mmol, obtained by base treatment of the hydrochloride and extracting the free base in dichloromethane), and N,N'-dicyclohexylcarbodiimide (DCC, 0.58 g, 2.81 mmol) in dichloromethane (10 mL) was stirred at room temperature for 2 hours under an argon atmosphere. The precipitated DCU was removed by filtration, and the dichloromethane solution was purified by column chromatography on silica gel (20 g) eluting with 0-25% methanol in dichloromethane. The product containing fractions were combined and concentrated under reduced pressure. The remaining gel was dried under high vacuum at room temperature until the weight was constant. The experiment produced 2-01 as an off-white gel (0.36 g, 27% yield). Its spectra are:

$^1$H NMR (300 MHz, CD$_3$OD): δ 5.68 (m, 1H), 3.87 (dd, 1H, J=14.1, 8.1 Hz), 3.73 (d, 1H, J=14.1 Hz), 3.21 (s, 9H), 2.63-2.56 (m, 3H), 2.10 (m, 1H), 1.83 (m, 2H), 1.63 (m, 4H), 1.34 (m, 4H), 1.19-1.14 (m, 6H), 0.84 (br s, 6H); and $^{13}$C NMR (75 MHz, CD$_3$OD): δ 177.14, 169.50, 69.82, 66.80, 54.83, 54.66, 51.78, 48.29, 43.84, 40.85, 40.69, 35.35, 33.38, 31.66, 30.87, 19.42, 19.15.

The isobutyric ester (2-01, 0.36 g, 0.76 mmol) was dissolved in anhydrous methanol (12 mL). Dry potassium carbonate (0.5 g, 3.61 mmol) was added and the mixture was vigorously stirred for 5 hours at room temperature under an argon atmosphere. The excess potassium carbonate was removed by filtration and the methanol solution was acidified with concentrated hydrochloric acid (1.0 mL) in methanol (20 mL). The methanol was concentrated under reduced pressure and the residual gel was dissolved in a small volume of DIUF water (5 mL) and purified on ODS-silica gel (20 g), eluting with 50% methanol in dilute hydrochloric acid (0.05%). The product containing fractions were combined and the volume was reduced by 50% under reduced pressure. The remaining aqueous portion was freeze-dried until a constant weight was achieved. The experiment generated 2 (0.18 g, 66% yield) as a colorless foam. Its spectra are:

$^1$H NMR (300 MHz, DMSO-d$_6$): δ 7.55 (s, 1H), 4.34 (m, 1H), 3.32 (d, 2H, J=5.4 Hz), 3.12 (s, 9H), 2.23 (m, 2H), 2.05 (m, 1H), 1.74 (br s, 2H), 1.56 (br s, 4H), 1.26 (m, 4H), 1.08 (br s, 2H), 0.79 (s, 6H);

$^{13}$C NMR (75 MHz, DMSO-d$_6$): δ 168.52, 69.72, 62.72, 53.36, 52.46, 52.35, 50.24, 46.99, 42.32, 41.78, 31.86, 30.16, 29.51;

HPLC analysis: 97.42% purity (at 205 nm), room temperature=8.107 min, 35% ACN, 65% phosphate buffer (0.25 mmol, pH=2.5), Gemini C18, 5μ, 4.6×259 mm (#262049-2), 1 mL/min., 40° C., 20 μL injection volume;

Specific rotation: $[α]_D^{25}$=−6.40 deg (25° C., c=0.0050 g×mL$^{-1}$, ethanol, 589 nm);

HRMS: LSIMS (FAB) [M—Cl$^-$]: theoretical 323.2693. found 323.2689; and

CHN analysis:
found: C, 55.06; H, 9.34; N, 6.71; Cl, 11.09.
calculated: C, 63.58; H, 9.83; N, 7.80; Cl, 9.88 (C$_{19}$H$_{35}$ClN$_2$O$_2$).
best fit: C, 54.96; H, 9.68; N, 6.66; Cl, 12.64 (C$_{19}$H$_{35}$ClN$_2$O$_2$+2.25H$_2$O+0.25 CH$_2$Cl$_2$, dichloromethane used in CHN sample preparation, not in original sample).

Example 3

3: {3-Benzyloxycarbonyl-(R)-2-[3-(1,3,3,5,5-pentamethyl-cyclohexylcarbamoyl)-propionyloxy]-propyl}-trimethylammonium bromide A mixture of the benzyl ester of L-carnitine (1-04, 5.0 g, 0.015 mol), succinic anhydride (10.0 g, 0.10 mol), pyridine (5 mL), and dichloromethane (3 mL) was stirred at room temperature for 20 hours, under an argon atmosphere. After 24 hours, the mixture was concentrated under reduced pressure and dried under high vacuum at room temperature until the weight was constant. The crude material (19.2 g) was purified by column chromatography on silica gel (100 g), eluting with methanol in dichloromethane (gradient 2-20%). The product containing fractions were combined, concentrated under reduced pressure, and dried under high vacuum at room temperature until the weight was constant. The experiment produced the succinic ester of L-carnitine benzyl ester (3-02, 2.73 g, 44% yield) as a light, brown foam. Its spectra are:

$^1$H NMR (300 MHz, CD$_3$OD): δ 7.38 (m, 5H), 5.70 (m, 1H), 5.16 (s, 2H), 3.91 (dd, 1H, J=14.4, 8.7 Hz), 3.77 (d, 1H, J=14.4 Hz), 3.22 (s, 9H), 2.87 (d, 2H, J=5.7 Hz), 2.68-2.42 (m, 4H); and $^{13}$C NMR (75 MHz, CD$_3$OD): δ 175.67, 173.34, 170.50, 137.05, 129.63, 129.48, 69.18, 68.11, 66.40, 54.83, 38.18, 30.31, 29.61.

A mixture of the succinic ester of L-carnitine benzyl ester (3-02, 0.91 g, 2.10 mmol), neramexane (0.34 g, 2.0 mmol)[1], and N,N'-dicyclohexylcarbodiimide (DCC, 0.42 g, 2.0 mmol) in dichloromethane (10 mL) was stirred at room temperature for 2 hours under an argon atmosphere. The precipitated DCU was removed by filtration, and the dichloromethane solution was purified twice by column chromatography on silica gel (25 g) eluting with 0-25% methanol in dichloromethane. The product containing fractions were combined and concentrated under reduced pressure. The remaining gel was dissolved in DIUF water (100 mL) and freeze-dried under high vacuum at room temperature until the weight was constant. The experiment produced 3-01 as an off-white gel (0.31 g, 28% yield). Its spectra are:

$^1$H NMR (300 MHz, CD$_3$OD): δ 7.37 (m, 5H), 7.03 (s, 1H), 5.67 (m, 1H), 5.16 (s, 2H), 3.93 (dd, 1H, J=14.4, 8.7 Hz), 3.78 (d, 1H, J=14.4 Hz), 3.24 (s, 9H), 2.87 (d, 2H, J=6.0 Hz), 2.56-2.38 (m, 4H), 2.25 (m, 2H), 1.30 (d, 2H, J=13.8 Hz), 1.25 (s, 3H), 1.10 (m, 6H), 1.00 (d, 2H, J=13.5 Hz), 0.88 (m, 6H);

$^{13}$C NMR (75 MHz, CD$_3$OD): δ 173.47, 173.37, 170.51, 137.02, 129.60, 129.56, 129.44, 69.11, 68.03, 66.30, 55.58, 54.80, 52.90, 48.37, 38.13, 36.81, 32.42, 32.32, 30.84, 30.37, 28.70, 28.58;

HPLC: Suitable HPLC conditions were not found for this compound;

Specific rotation: $[α]_D^{25}$=−4.5 deg (25° C., c=0.0011 g×mL$^{-1}$, ethanol, 589 nm);

HRMS: LSIMS (FAB) [M-Br$^-$]$^+$: theoretical: 503.3479. found: 503.3469; and

CHN analysis:
found: C, 54.59; H, 8.10; N, 5.61.
calculated: C, 64.60; H, 8.79; N, 5.20 (C$_{29}$H$_{47}$BrN$_2$O$_5$).
best fit: C, 54.63; H, 8.38; N, 4.39 (C$_{29}$H$_{47}$BrN$_2$O$_5$+ 3H$_2$O).

Example 4

4-01: {3-Benzyloxycarbonyl-(R)-2-[3-(3,5-Dimethyladamantan-1-ylcarbamoyl)-propionyloxy]-propyl}-trimethylammonium bromide A mixture of the succinic ester of L-carnitine benzyl ester (3-02, 0.6 g, 1.38 mmol), memantine (0.25 g, 1.38 mmol), and N,N'-dicyclohexylcarbodiimide (DCC, 0.28 g, 1.38 mmol) in dichloromethane (5 mL) was stirred at room temperature for 4 hours under an argon atmosphere. The precipitated DCU was removed by filtration, and the dichloromethane solution was purified twice by column chromatography on silica gel (25 g) eluting with 0-25% methanol in dichloromethane. The product containing fractions were combined and concentrated under reduced pressure. The remaining gel was dissolved in DIUF water (100 mL) and freeze-dried under high vacuum at room temperature until the weight was constant. The experiment produced 4-01 as an off-white gel (0.24 g, 29% yield). Its spectra are:

$^1$H NMR (300 MHz, CD$_3$OD): δ 7.37 (m, 6H), 5.68 (m, 1H), 5.16 (s, 2H), 3.96 (dd, 1H, J=14.1, 8.7 Hz), 3.78 (d, 1H, J=14.1 Hz), 3.24 (s, 9H), 2.88 (d, 2H, J=6.3 Hz), 2.56-2.38 (m, 4H), 2.09 (m, 1H), 1.83 (m, 2H), 1.62 (m, 4H), 1.39-1.26 (m, 4H), 1.13 (br s, 2H), 0.83 (s, 6H);

$^{13}$C NMR (75 MHz, CD$_3$OD): δ 173.40, 172.89, 170.51, 137.00, 129.61, 129.57, 129.44, 69.13, 68.04, 66.29, 54.79, 54.56, 51.78, 48.44, 43.84, 40.92, 38.15, 33.33, 31.90, 31.61, 30.92, 30.66, 27.09, 26.19;

HPLC: Suitable HPLC conditions were not found for this compound;

Specific rotation: $[\alpha]_D^{25}$=−2.0 deg (25° C., c=0.0022 g×mL$^{-1}$, ethanol, 589 nm);

HRMS: LSIMS (FAB) [M-Br$^-$]$^+$: theoretical: 513.3323. found: 513.3315; and

CHN analysis:
found: C, 56.54; H, 8.01; N, 4.66.
calculated: C, 65.62; H, 8.26; N, 5.10 (C$_{30}$H$_{45}$BrN$_2$O$_5$).
best fit: C, 56.42; H, 7.89; N, 4.39 (C$_{30}$H$_{45}$BrN$_2$O$_5$+ 2.5H$_2$O).

Although the invention has been described with reference to its preferred embodiments, those of ordinary skill in the art may, upon reading and understanding this disclosure, appreciate changes and modifications which may be made which do not depart from the scope and spirit of the invention as described above or claimed hereafter.

What is claimed is:

1. A compound, or its pharmaceutically-acceptable salts, of Formula (I) below,

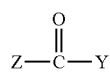

Formula (I)

wherein:

Z is a trialicyclic adamantane as shown by Formulae (A),

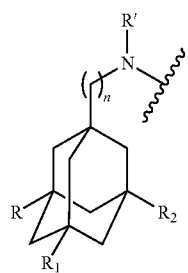

(A)

wherein:
R, R$_1$, and R$_2$ are each independently H or CH$_3$;
C$_1$-C$_6$ straight chain or branched alkyls, C$_3$-C$_6$ cycloalkyl, C$_2$-C$_6$ alkenyl, C$_2$-C$_6$ alkynyl; C$_6$-C$_{10}$ aryl unsubstituted or substituted with straight chain or branched C$_1$-C$_6$ alkyl, C$_1$-C$_6$ alkoxyl, 1,3-dioxolanyl, cyano, halo, nitro, trihaloalkyl, C$_1$-C$_6$ acyl, C$_1$-C$_6$, dialkylamino, C$_1$-C$_6$ acylamino, C$_1$-C$_6$ mercaptoalkyl; alkylaryl (C$_6$-C$_{10}$), such as a benzyl group unsubstituted or substituted with straight chain or branched C$_1$-C$_6$ alkyl, C$_1$-C$_6$ alkoxyl, 1,3-dioxolanyl, cyano, halo, trihaloalkyl, C$_1$-C$_6$ acyl, C$_1$-C$_6$ dialkylamino, and C$_1$-C$_6$ mercaptoalkyl; and alkyldiaryls such as diphenylmethyl in which the aryls may be bridged by —CH$_2$—CH$_2$— or O or S, where the alkyldiaryls may be unsubstituted or substituted with straight chain or branched C$_1$-C$_6$ alkyl, C$_1$-C$_6$ alkoxyl, 1,3-dioxolanyl, cyano, halo, trihaloalkyl, C$_1$-C$_6$ acyl, C$_1$-C$_6$ dialkylamino, and C$_1$-C$_6$ mercaptoalkyl;

n=0 or an integer from 1 through 6;

Ŕ is H or C$_1$-C$_4$ straight-chain alkyl;

Y is a moiety of Formulae (D), and shown below,

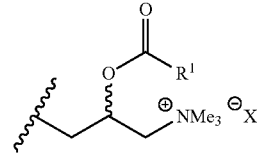

(D)

wherein:

R$^1$ is independently selected from the group consisting of straight or branched chain C$_1$-C$_6$ alkyl, C$_3$-C$_6$ cycloalkyl; C$_2$-C$_6$ alkenyl; C$_2$-C$_6$ alkynyl; C$_6$-C$_{10}$ aryl such as phenyl, naphthyl, and the like, or a heteroaryl such as furanyl, imidazolyl, pyrollyl, triazolyl, pyridyl, and the like, unsubstituted or substituted with one or more straight chain or branched C$_1$-C$_6$ alkyl, C$_1$-C$_6$ alkoxyl, 1,3-dioxolanyl, cyano, halo, nitro, trihaloalkyl, C$_1$-C$_6$ acyl, C$_1$-C$_6$ dialkylamino, C$_1$-C$_6$ acylamino, C$_1$-C$_6$ mercaptoalkyl; and straight or branched chain alkylaryl (C$_6$-C$_{10}$), such as a benzyl group, or an alkyl heteroaryl wherein the aryl or the hetroaryl group may be unsubstituted or substituted with one or more straight chain or branched C$_1$-C$_6$ alkyl, C$_1$-C$_6$ alkoxyl, 1,3-dioxolanyl, cyano, halo, trihaloalkyl, C$_1$-C$_6$ acyl, C$_1$-C$_6$ dialkylamino, and C$_1$-C$_6$ mercaptoalkyl, and alkyldiaryls such as diphenylmethyl in which the aryls may be bridged by —CH$_2$—CH$_2$— or O or S, where the alkyldiaryls may be unsubstituted or substituted with straight chain or branched C$_1$-C$_6$ alkyl, C$_1$-C$_6$ alkoxyl, 1,3-dioxolanyl, cyano, halo, trihaloalkyl, C$_1$-C$_6$ acyl, C$_1$-C$_6$ dialkylamino, and C$_1$-C$_6$ mercaptoalkyl; and X$^-$ is a pharmaceutically-acceptable inorganic or organic counter ion.

2. The compound of Formula (I) as defined in claim 1 wherein R and Ŕ of Formula (I) are H and the subset of compounds are those of Formula 3 as shown below,

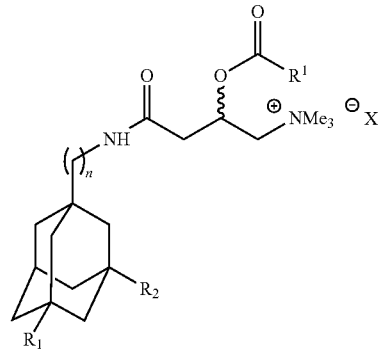

Formula 3 wherein:

$R_1$ and $R_2$ are H or $CH_3$;

$X^-$ is any pharmaceutically-acceptable organic or inorganic counter ion;

n=0, or an integer from 1 through 6;

$R^1$ is independently selected from the group consisting of straight or branched chain $C_1$-$C_6$ alkyl, $C_3$-$C_6$ cycloalkyl; $C_2$-$C_6$ alkenyl; alkynyl; $C_6$-$C_{10}$ aryl such as phenyl, naphthyl and the like, or a heteroaryl such as furanyl, imidazolyl, pyrollyl, triazolyl, pyridyl or the like, unsubstituted or substituted with one or more straight chain or branched $C_1$-$C_6$ alkyl, $C_1$-$C_6$ alkoxyl, 1,3-dioxolanyl, cyano, halo, nitro, trihaloalkyl, $C_1$-$C_6$ acyl, $C_1$-$C_6$ dialkylamino, $C_1$-$C_6$ acylamino, $C_1$-$C_6$ mercaptoalkyl; and straight or branched chain alkylaryl ($C_6$-$C_{10}$), such as a benzyl group, or an alkyl heteroaryl wherein the aryl or the hetroaryl group may be unsubstituted or substituted with one or more straight chain or branched $C_1$-$C_6$ alkyl, $C_1$-$C_6$ alkoxyl, 1,3-dioxolanyl, cyano, halo, trihaloalkyl, $C_1$-$C_6$ acyl, $C_1$-$C_6$ dialkylamino, and $C_1$-$C_6$ mercaptoalkyl, and alkyldiaryls such as diphenylmethyl in which the aryls may be bridged by —$CH_2$—$CH_2$— or O or S, where the alkyldiaryls may be unsubstituted or substituted with straight chain or branched $C_1$-$C_6$ alkyl, $C_1$-$C_6$ alkoxyl, 1,3-dioxolanyl, cyano, halo, trihaloalkyl, $C_1$-$C_6$ acyl, $C_1$-$C_6$ dialkylamino, and $C_1$-$C_6$ mercaptoalkyl.

3. The compound of Formula 1 as defined in claim 2 wherein the compounds are those of Formula 3(A) below and its pharmaceutically-acceptable salts,

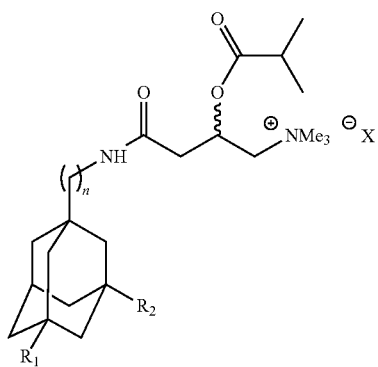

Formula 3(A)

wherein:

$R_1$ and $R_2$ are H or $CH_3$;

n=0 or 1;

$X^-$ is any of the pharmaceutically-acceptable counter ions, and $R^1$ is an isopropyl moiety;

as a single stereoisomer, D-(S)— or L-(R)—, or as a mixture of both isomers.

4. The compound of Formula 1 as defined in claim 2 wherein the compounds are those of Formula 3(B) below and its pharmaceutically-acceptable salts,

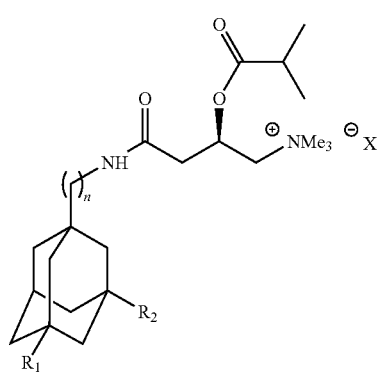

Formula 3(B)

wherein:

$R_1$ and $R_2$ are H or $CH_3$;

n=0 or 1;

$X^-$ is any of the pharmaceutically-acceptable counter ions; and $R^1$ is an isopropyl moiety;

as a single stereoisomer of L-(R)— configuration.

5. Pharmaceutical formulations containing at least one of the compounds defined in any one of claims 1 and 2-4 as an active substance, in the form of tablets, capsules, solutions as syrups and elixirs, suspensions, long acting, slow release depot forms made up of granules, liposomes, ointments, patches; injections for intravenous, intramuscular subcutaneous, intraperitoneal administration, solid nanodispersions for oral or intranasal delivery, and suppositories for vaginal and rectal administration.

6. A formulation of claim 5 wherein the active substance is present in an effective amount in a single or multiple doses.

* * * * *